US012690876B2

(12) United States Patent
Buerk et al.

(10) Patent No.: US 12,690,876 B2
(45) Date of Patent: Jul. 28, 2026

(54) SURGICAL INSTRUMENT AND TOOL FOR A SURGICAL INSTRUMENT

(71) Applicant: Aesculap AG, Tuttlingen (DE)

(72) Inventors: André Buerk, Villingen-Schwenningen (DE); Roland-Alois Hoegerle, Tuttlingen (DE); Frederick Lenzenhuber, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 897 days.

(21) Appl. No.: 17/913,912

(22) PCT Filed: Mar. 25, 2021

(86) PCT No.: PCT/EP2021/057745
§ 371 (c)(1),
(2) Date: Sep. 23, 2022

(87) PCT Pub. No.: WO2021/191352
PCT Pub. Date: Sep. 30, 2021

(65) Prior Publication Data
US 2024/0206886 A1      Jun. 27, 2024

(30) Foreign Application Priority Data
Mar. 25, 2020    (DE) .................... 10 2020 108 275.4

(51) Int. Cl.
*A61B 17/16*        (2006.01)
*A61B 90/98*        (2016.01)
*A61B 17/00*        (2006.01)

(52) U.S. Cl.
CPC ........ *A61B 17/1626* (2013.01); *A61B 17/162* (2013.01); *A61B 17/1633* (2013.01);
(Continued)

(58) Field of Classification Search
CPC .......... A61B 2017/00039; A61B 17/16; A61B 17/1626; A61B 17/1633; A61B 90/90; A61B 90/96; A61B 90/98
See application file for complete search history.

(56) References Cited

U.S. PATENT DOCUMENTS 9,707,026 B2     7/2017  Malackowski et al.
2003/0199856 A1   10/2003  Hill et al.
(Continued)

FOREIGN PATENT DOCUMENTS

CN        105813592 A      7/2016
CN        108852443 A     11/2018
(Continued)

OTHER PUBLICATIONS

Office Action received in Japanese Application No. 2022-557973 dated Jun. 23, 2025, with translation, 9 pages.
(Continued)

*Primary Examiner* — Larry E Waggle, Jr.
(74) *Attorney, Agent, or Firm* — Christopher A. Rothe; CM Law

(57)        ABSTRACT

A surgical instrument, a spacer sleeve for a surgical instrument, and a tool for a surgical instrument. The surgical instrument includes the sleeve, which is designed to receive a part of the tool. The sleeve has signal lines that extend axially along the sleeve. A magnetic memory output device is arranged on the sleeve and is electrically connected to the signal lines. The magnetic memory output device outputs information about the tool based on information contained in a magnetic memory surrounding a circumference of the part of the tool. The magnetic memory output device also transfers information to an analysis unit via the signal lines of the sleeve.

13 Claims, 15 Drawing Sheets

(52) U.S. Cl.
      CPC .... *A61B 90/98* (2016.02); *A61B 2017/00039*
              (2013.01); *A61B 2017/1602* (2013.01)

(56) References Cited

U.S. PATENT DOCUMENTS

| | | | |
|---|---|---|---|
| 2018/0000557 A1* | 1/2018 | Brandstaetter | A61B 90/98 |
| 2019/0059983 A1 | 2/2019 | Germain et al. | |
| 2019/0328448 A1 | 10/2019 | Germain et al. | |
| 2020/0390519 A1 | 12/2020 | Brandstaetter et al. | |
| 2022/0133394 A1 | 5/2022 | Benamou et al. | |
| 2023/0037993 A1 | 2/2023 | Krueger et al. | |

FOREIGN PATENT DOCUMENTS

| | | | |
|---|---|---|---|
| DE | 102006057338 A1 | 6/2008 | |
| EP | 2647339 A1 | 10/2013 | |
| EP | 3266410 A1 | 1/2018 | |
| EP | 3505078 A2 | 7/2019 | |
| JP | 2001112774 A | 4/2001 | |
| JP | 2009153989 A | 7/2009 | |
| JP | 2019514481 A | 6/2019 | |

OTHER PUBLICATIONS

Office Action received in Japanese Application No. 2022-557973 dated Nov. 29, 2024, with translation, 8 pages.
Search Report received in German Application No. 10 2020 108 275.4 dated Jan. 20, 2021, with translation, 11 pages.
Search Report received in International Application No. PCT/EP2021/057745 dated Jun. 21, 2021, with translation, 6 pages.
Written Opinion received in International Application No. PCT/EP2021/057745 dated Jun. 21, 2021, with translation, 9 pages.
Office Action received in Chinese Application No. 202180023269 dated Jan. 29, 2026, with translation, 18 pages.

\* cited by examiner

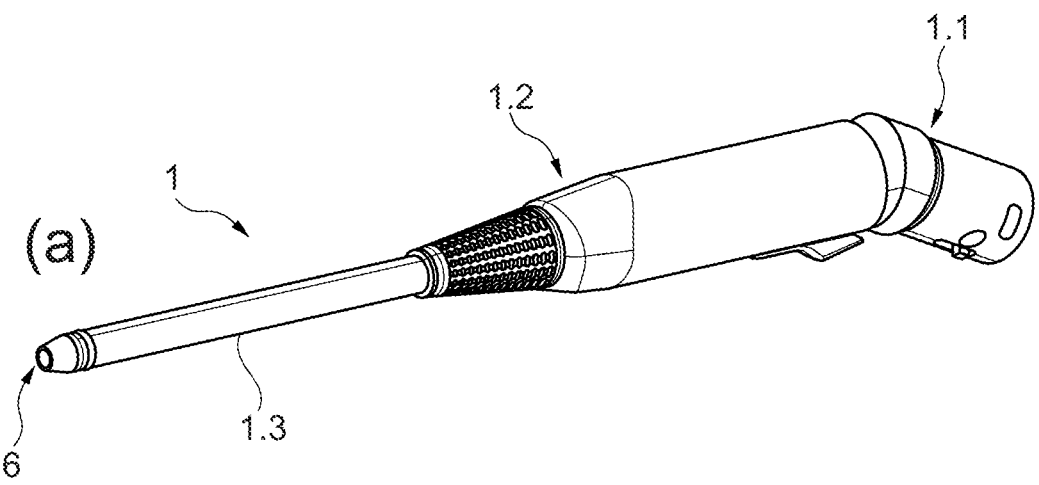
(a)
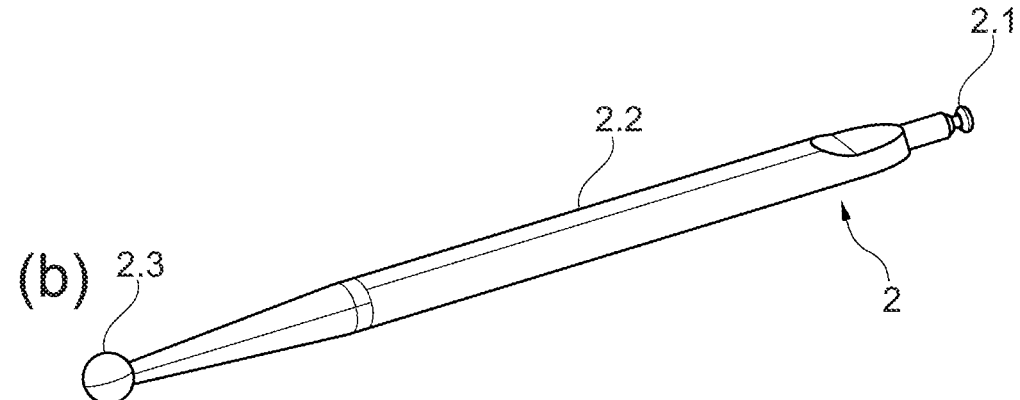
(b)
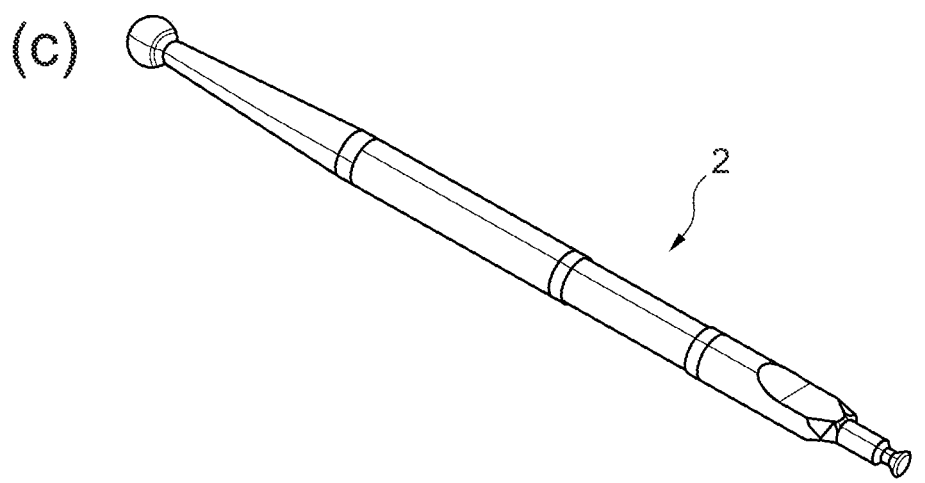
(c)
Fig. 1

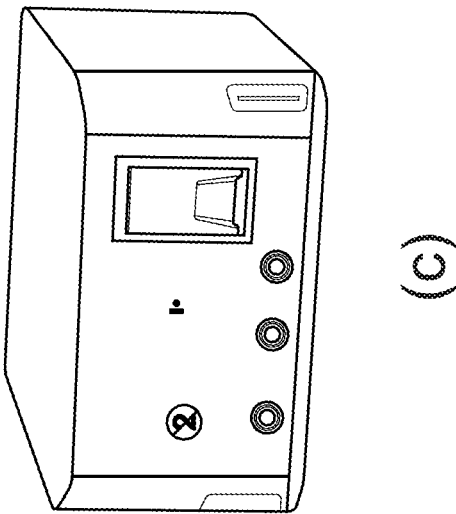
(c)
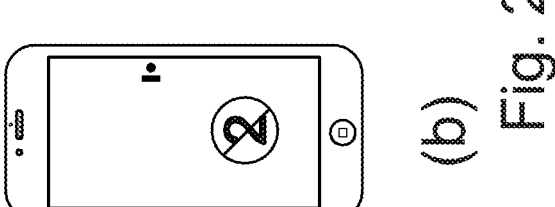
(b)
Fig. 2
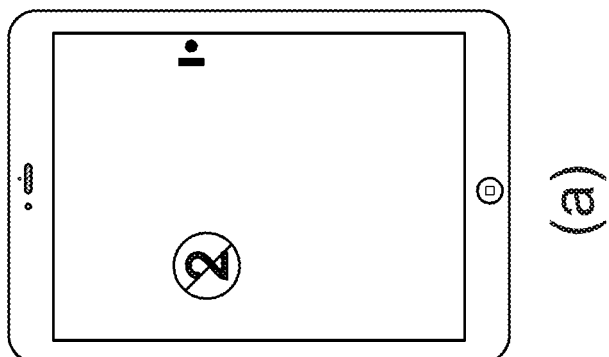
(a)

(a)
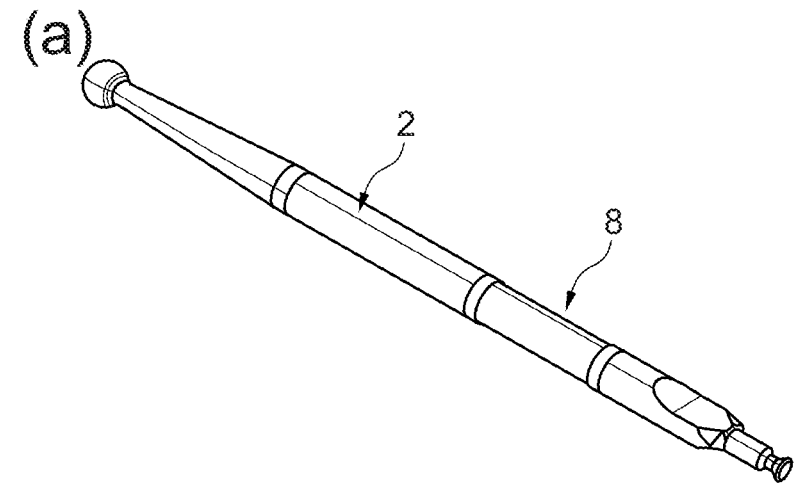
(b)
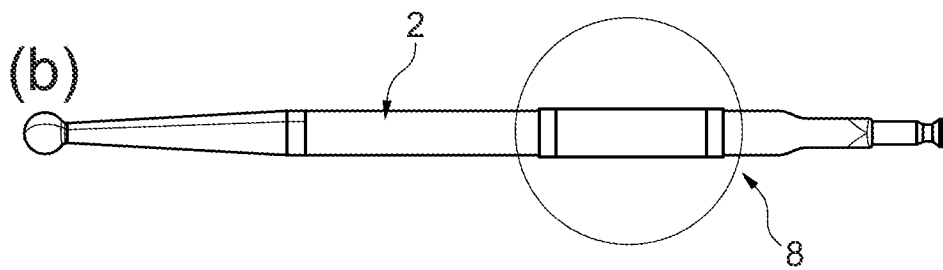
(c)
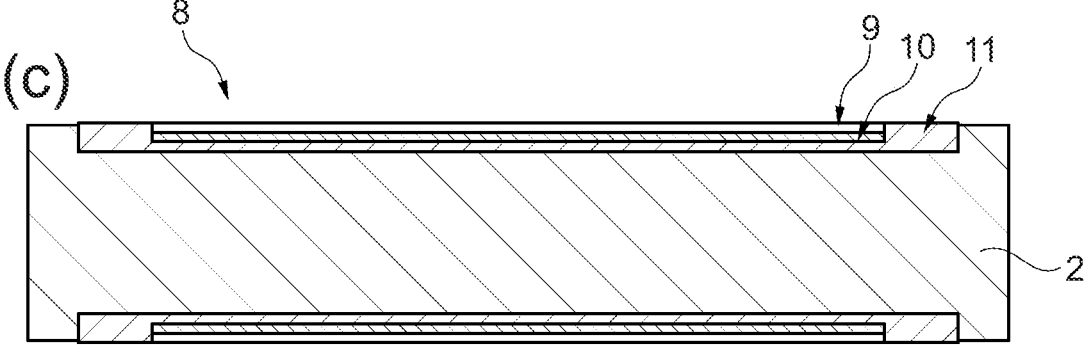
Fig. 4

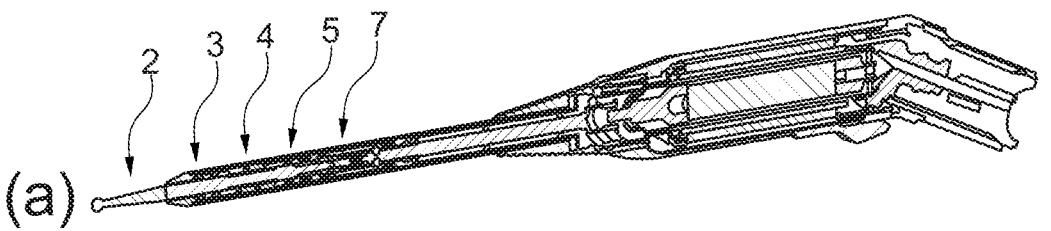
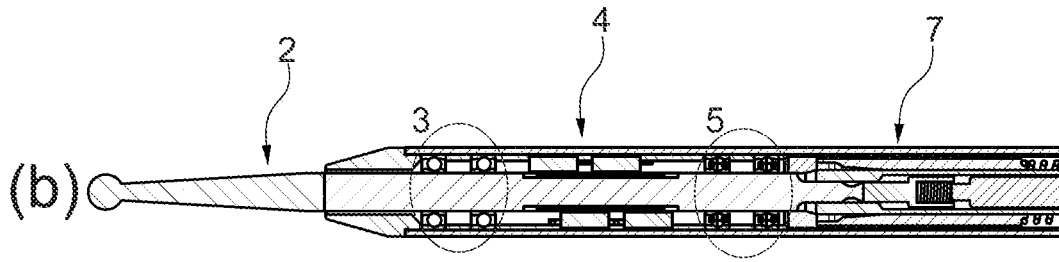
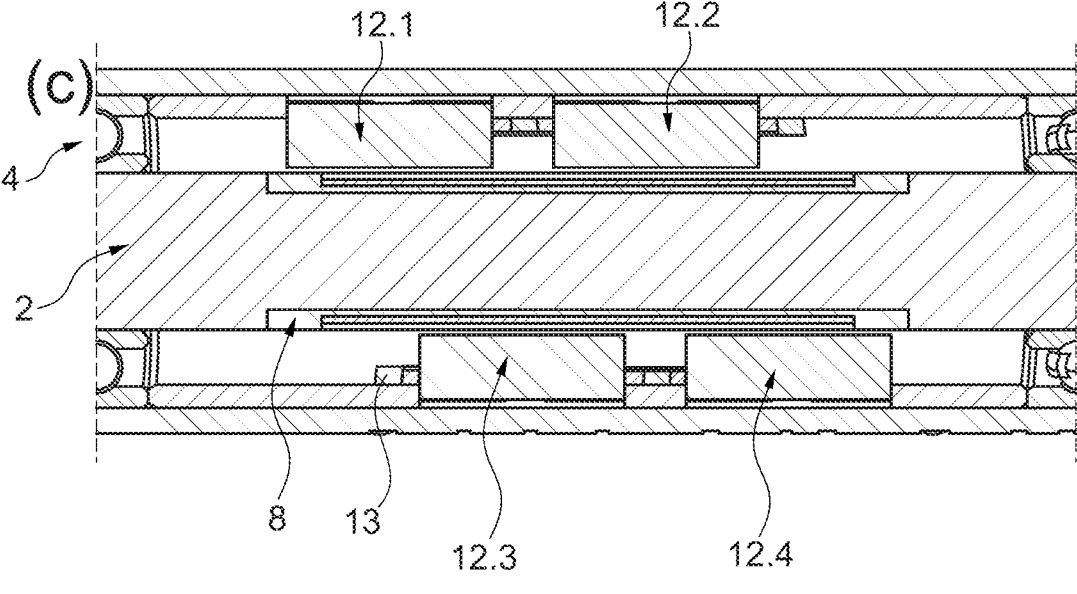
Fig. 5

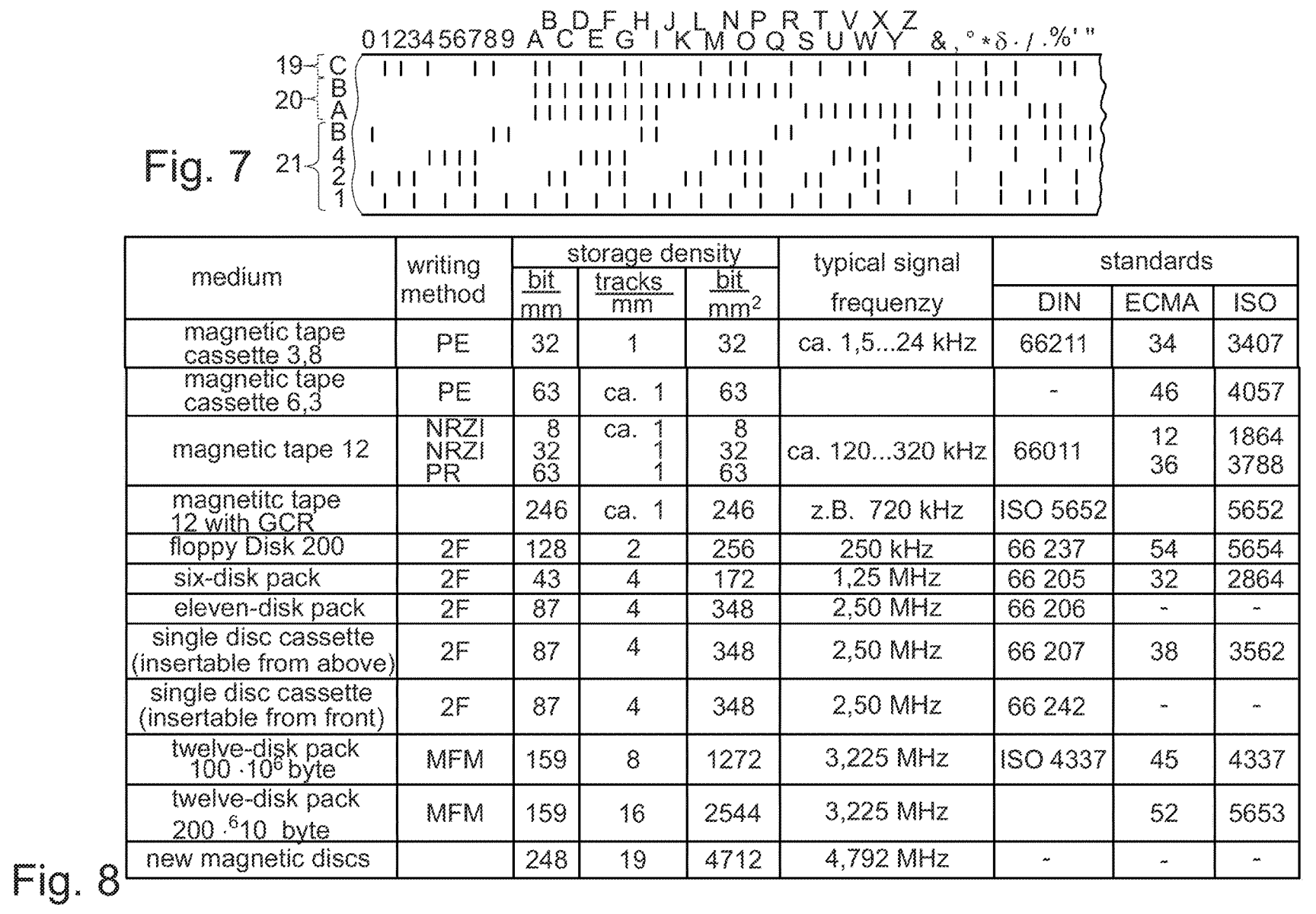

| medium | writing method | storage density | | | typical signal frequenzy | standards | | |
|---|---|---|---|---|---|---|---|---|
| | | bit/mm | tracks/mm | bit/mm² | | DIN | ECMA | ISO |
| magnetic tape cassette 3,8 | PE | 32 | 1 | 32 | ca. 1,5...24 kHz | 66211 | 34 | 3407 |
| magnetic tape cassette 6,3 | PE | 63 | ca. 1 | 63 | | - | 46 | 4057 |
| magnetic tape 12 | NRZI / NRZI / PR | 8 / 32 / 63 | ca. 1 | 8 / 32 / 63 | ca. 120...320 kHz | 66011 | 12 / 36 | 1864 / 3788 |
| magnetic tape 12 with GCR | | 246 | ca. 1 | 246 | z.B. 720 kHz | ISO 5652 | | 5652 |
| floppy Disk 200 | 2F | 128 | 2 | 256 | 250 kHz | 66 237 | 54 | 5654 |
| six-disk pack | 2F | 43 | 4 | 172 | 1,25 MHz | 66 205 | 32 | 2864 |
| eleven-disk pack | 2F | 87 | 4 | 348 | 2,50 MHz | 66 206 | - | - |
| single disc cassette (insertable from above) | 2F | 87 | 4 | 348 | 2,50 MHz | 66 207 | 38 | 3562 |
| single disc cassette (insertable from front) | 2F | 87 | 4 | 348 | 2,50 MHz | 66 242 | - | - |
| twelve-disk pack 100·10⁶ byte | MFM | 159 | 8 | 1272 | 3,225 MHz | ISO 4337 | 45 | 4337 |
| twelve-disk pack 200·⁶10 byte | MFM | 159 | 16 | 2544 | 3,225 MHz | | 52 | 5653 |
| new magnetic discs | | 248 | 19 | 4712 | 4,792 MHz | - | - | - |

Fig. 8

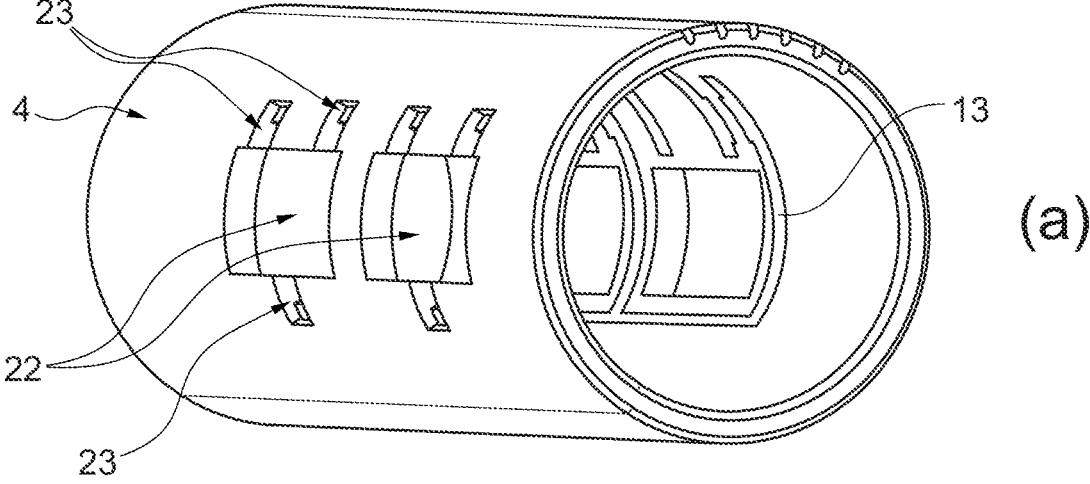
(a)
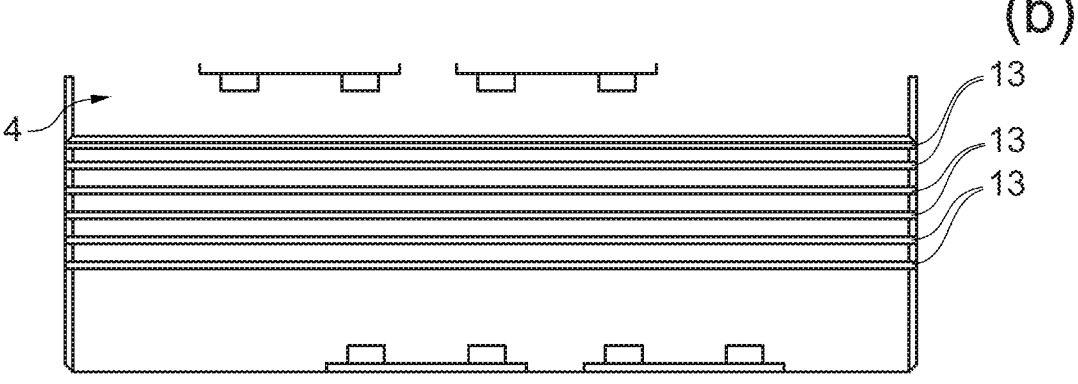
(b)
Fig. 10

(a)
(b)
(c)
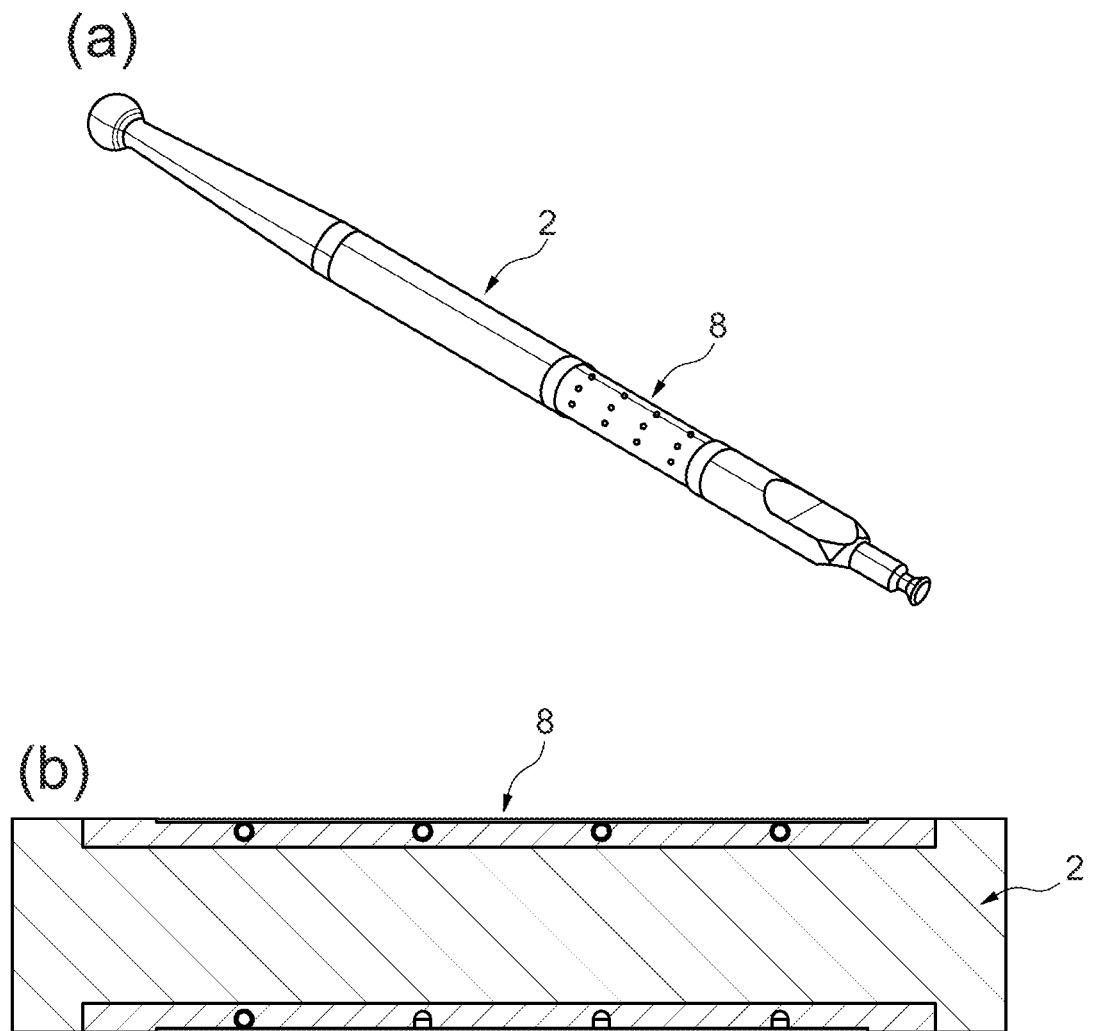
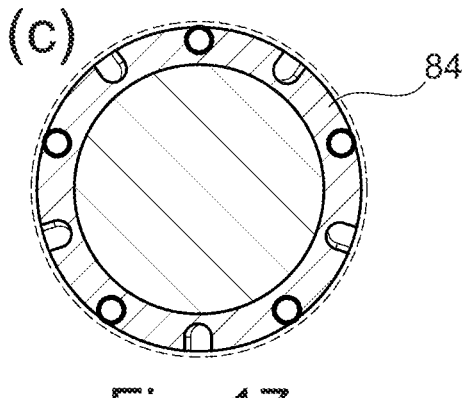
Fig. 17

SURGICAL INSTRUMENT AND TOOL FOR A SURGICAL INSTRUMENT

CROSS-REFERENCE TO RELATED APPLICATIONS

This application is the United States national stage entry of International Application No. PCT/EP2021/057745, filed Mar. 25, 2021, and claims priority to German Application No. 10 2020 108 275.4, filed Mar. 25, 2020.

FIELD

The invention relates to a surgical instrument, in particular a milling handpiece, and a tool for the surgical instrument.

BACKGROUND

Up to now, in the field of non-medical electrical hand-held machine tools, which also include milling machines, devices for automatic recognition of tool-specific data of tools which can be inserted into the hand-held machine tool have been known, in which a tool such as a cutting drill or the like has a geometric coding, for example a bar coding, in the region of its insertion shaft. Signals corresponding to the coding are generated via a reading device, such as an electronic, optical or mechanical sensor, installed in the tool holder (tool chuck) and aligned with the coding, and are transmitted to a control device or evaluation unit of the tool machine for further processing.

In particular, tools used in the medical field, such as cutting, drilling and/or milling tools, are essentially divided into three sections: a proximal coupling portion, a shaft portion and at least one distal working end/effector. The shaft portion connects the coupling portion to the working end of the tool. The working end is opposite the coupling portion at the other end of the tool and is the functional part of the tool for engaging with a patient. This may be shaped in a variety of application-specific ways. Tools of the type referred to herein include tools generally usable in the field of medicine, drills, milling cutters and the like. However, there is no restriction to products of the aforementioned type from the medical field in particular.

In the field of medicine, due to the type of tools used and the conditions of the respective working environments, it is neither feasible nor practical to use the above-mentioned coupled coding system; instead, labels or stickers have been used up to now, which can be arranged on the tool itself or on the outer packaging of the tool. In order to identify, for example, which tool is inserted in the instrument used, the label of the or respectively of each individual tool or its outer packaging has to be viewed. Up to now, there has been no automatic and/or automatically documenting tool identification, so that a user or customer has to identify from labels or inscribing labels, or can only identify from them, which product it is, and then has to document it manually.

This has a negative impact on users, distributors, customers and manufacturers of such tools. Among other things, a user or customer of such a tool cannot easily recognize whether an intended tool is suitable for his specific application or not without viewing the label or outer packaging, respectively. For example, a distributor or customer usually cannot determine which product inventories are still at a warehouse or consignment store without taking inventory. A manufacturer, for example, cannot determine which products have been combined and/or used. Consequently, an overload of tools and possibly associated product damage cannot be traced. Thus, no customized logistics can be provided for the customer.

One of the reasons for this problem is that electromotive, hydraulic or pneumatic drive handpieces are equipped with a generally replaceable spacer sleeve at their distal end portion so that they can be adapted to the patient's anatomy, wherein their distal end portion is prepared for rotatable and/or displaceable mounting of the tool. In contrast to the handpiece, the spacer sleeve is small in diameter so that it can be inserted into the abdominal cavity of a patient, for example. In order to drive the tool, a torque rod is also mounted in the spacer sleeve, which transmits a drive torque from the handpiece-internal drive motor to the tool.

Therefore, in particular in the field of medicine, there is a need for automatic identification of tools, such as drills, milling cutters and the like, via which the aforementioned disadvantages are eliminated and associated problems are solved.

SUMMARY

Thus, it is the object of the invention to avoid or at least reduce the disadvantages arising from the prior art. In particular, a tool engaged with a surgical instrument is to be automatically detected.

This object is solved in a generic device according to the invention by providing a spacer sleeve for a surgical instrument and preferably a surgical instrument with such a spacer sleeve, wherein the sleeve is configured at its distal end region to receive at least a part of a tool, preferably rotatably. The sleeve has signal lines. The signal lines run axially along the sleeve. The spacer sleeve (or the surgical instrument) further comprises a magnetic memory readout device. The magnetic memory readout device is arranged on the sleeve. The magnetic memory read-out device is electrically connected to the signal lines of the sleeve. The magnetic memory read-out device is configured to read out, based on a magnetic memory, information contained in the magnetic memory about the tool. The magnetic memory surrounds or forms a circumference of the part of the tool. The magnetic memory readout device is further configured to transmit the readout information to an evaluation unit via the signal lines of the sleeve.

In other words, a tool according to the present invention has a tool information carrier, preferably a magnetic memory, which is arranged in the shaft portion of the tool and contains tool-specific information. A readout device is arranged in/on the spacer sleeve in the distal tool receiving area, which is configured to read out the tool information carrier (already) inserted in the spacer sleeve and its information. (Objective) data transmission lines/signal lines (conductor tracks) are connected to the readout device, which are laid in/on the spacer sleeve in its longitudinal direction and preferably lead into a coupling portion of the spacer sleeve with the handpiece. Via these signal lines, the readout device is connected to an evaluation unit, preferably in the handpiece, or it is connectable to the handpiece by coupling the spacer sleeve.

This means that information about the tool can be obtained automatically via the read-out device and can be evaluated by the evaluation unit. The surgeon can therefore obtain information about the tool used/inserted in the spacer sleeve without prior inspection.

The surgical instrument may be a surgical motor instrument, such as a milling handpiece. In particular, as used herein, the instrument is understood to be a surgical device intended to receive and operate the tool.

The sleeve may be made of an electrically non-conductive material. Furthermore, the material of the sleeve may be a hard material, for example ceramic.

The magnetic memory may contain information linked to the tool in the form of a layer. This information may be stored on the layer in the form of magnetization. This information may be arranged or stored at least in the circumferential direction or direction of rotation of the tool. The magnetic memory may comprise a ferromagnetic layer, which may be provided for magnetization.

The magnetic memory readout device may, for example, have a read head. The read head or the magnetic memory readout device may be configured to receive this information in the form of signals when the tool is rotated along a (magnetic) track in the circumferential direction of the tool shaft and to transmit this information via the signal lines. These signals can be based on a magnetic field that varies along the track due to the differently magnetized areas of the magnetic memory. This magnetic field can cause different voltages in the read head or the magnetic memory readout device, respectively, which can be transmitted as the information or signals via the signal lines.

The evaluation unit may be a processing unit internal or external to the surgical instrument. The evaluation unit may be configured to evaluate/process the information or signals. Via a user interface, the processing unit can output the corresponding results from the evaluation of the information or signals to a user of the surgical instrument.

The magnetic memory readout device may be located within a space defined by an outer sheath of the sleeve. Thus, the tool and the magnetic memory readout device can be housed together within the sleeve. Accordingly, the surgical instrument can be configured to save space.

The magnetic memory readout device may include at least one magnetometer. The magnetometer can act as the readout head defined above. The sleeve may have at least one recess/cut-out/window in its circumferential wall. The recess may include a portion of the magnetometer. The cut-out (through opening) may provide easy attachment of the magnetic memory readout device. Furthermore, this can ensure sufficient distance between the magnetometer and the magnetic memory of the tool during operation.

Advantageously, the magnetometer can be a Hall sensor in the form of a surface mounted device (SMD). This allows the magnetometer to be easily inserted into the sleeve, for example manually via clamping.

Reading can take place upon actuation of the surgical instrument (of the drive motor housed therein), for example via a toggle switch on the surgical instrument or an actuation switch connected to the surgical instrument, for example a foot pedal. Such an actuating device/actuating switch may be configured to put the surgical instrument into operation, in particular its motor. Thus, the user of the surgical instrument can be provided with information about the currently used tool by simply actuating an actuating element associated with the surgical instrument, such as a foot pedal.

The object defined above is solved in a generic device according to the invention in that a tool for a surgical instrument is provided. The tool comprises a part (tool shaft) intended to be received in a sleeve of a surgical instrument. The tool further comprises a data/information carrier, preferably a magnetic memory, in particular in the form of a layer. The (magnetic) layer is configured to form a circumference of the part, or respectively to cover an outer side of the tool shaft in its (entire) circumferential direction. The tool is adapted to interact with the surgical instrument or its spacer sleeve as defined above such that the magnetic memory is read out via a magnetic memory readout device of the surgical instrument/spacer sleeve. Thus, the information about the tool can be obtained and evaluated automatically. The surgeon can thus be enabled to obtain information about the tool used without prior inspection.

The magnetic memory can be configured to be slid onto the part. This allows a modular magnetic memory to be provided in optional connection with the tool.

The magnetic memory may comprise magnetized wire rings surrounding the circumference of the part. The wire rings can be arranged axially offset from each other along the tool.

Furthermore, the magnetic memory may have permanent magnets or wire pieces. The permanent magnets or wire pieces may be spaced from each other in the circumferential direction of the tool and in the axial direction along the tool.

In addition, the magnetic memory may have spherical permanent magnets. The spherical permanent magnets may be arranged offset from each other in the circumferential direction of the tool and in the axial direction along the tool.

Thus, different magnetic memory variants can be provided, with which information about the tool can be read out automatically via the magnetic memory readout device during operation of the surgical instrument.

The signal lines may be made of (good) conductive material, such as copper, silver or gold.

The sleeve is preferably arranged to pass or transmit electrical signals in an axial direction between a first (distal) axial end and a second (proximal) axial end of the sleeve and/or in a radial direction between an inner-sheath surface and an outer sheath surface of the sleeve.

Advantageously, an outer sheath surface of the sleeve has passages that extend over an entire axial length of the sleeve. Preferably, the signal lines are provided or respectively arranged in the passages. In other words, there is conductive material in the passages. This advantageously ensures that electrical signals can be tapped at the outer sheath surface of the sleeve, or respectively can be forwarded or transmitted.

The passages are preferably configured to be fine or filigree and are produced by grinding or engraving, for example laser engraving. The passages are preferably metallized and coated with a highly conductive material in order to configure the signal lines.

It is advantageous if the signal lines are offset inwards with respect to the outer sheath surface of the sleeve, so that the signal lines are provided only in a lower region of the groove. In other words, the signal lines are preferably completely countersunk in the passages so that the (outer) outer sheath surface of the sleeve is spaced from the signal lines in the radial direction of the sleeve. Thus, the signal lines are preferably not flush with the outer sheath surface, but are located further inside. This ensures that the individual signal lines are electrically separated from each other. This is necessary in particular since an outer tube of a milling handpiece, in which the sleeve is preferably to be inserted and against which the sleeve directly abuts, is often made of metal.

It is practical if an insulator is arranged above the signal lines. In other words, the aforementioned electrical separation of the signal lines from each other can be improved if an insulator is also provided. The insulator may, for example, be an insert, for example made of silicone. Alternatively, the insulator may also be implemented via an adhesive layer, for example. The additional insulation makes the surgical instrument, in particular the milling handpiece in which the sleeve is inserted, less sensitive to penetrating conductive liquids (e.g. a saline solution).

An advantageous configuration example is characterized in that an inner-sheath surface of the sleeve has at least one signal line. If signal lines are additionally or alternatively provided on the inner-sheath surface of the sleeve, electrical signals can be tapped in the inner-sheath surface, or can be forwarded or transmitted, respectively. For example, metallized tracks (at least one metallized track) may be provided on the inner-sheath surface. These metallized tracks can be connected to the magnetic memory readout device.

It is of particular advantage if signal lines provided on an inner-sheath surface of the sleeve are connected in an electrically conducting manner to corresponding signal lines provided on an outer sheath surface of the sleeve. For example, the sleeve may have fine bores (micro-bores) which extend in the radial direction of the sleeve and via which signal lines on the inner-sheath surface can be connected in an electrically conducting manner to respective signal lines on the outer sheath surface (for example via conducting material in the bores). In other words, the holes (micro bores) preferably run between the passages on the outer sheath surface and the signal lines on the inner-sheath surface. In other words, through-connections are preferably created as in printed circuit board technology, which at the same time can also function as solder pads. This means that wired components can also be integrated into the system, for example capacitors. Soldering points for SMD components of the magnetic memory readout device may be provided on the inner-sheath surface. These can be connected to the internal signal lines accordingly.

The signal lines can generally be incorporated into the sleeve at different depths. In this way, a sleeve with very thin walls can be realized, at least in sections. Furthermore, a large number of signal lines can be provided which are incorporated at different depths in the sleeve. This applies both to signal lines attached to the outer sheath surface and to those attached to the inner sheath surface. Preferably, the signal lines attached to the inner-sheath surface lie on the inner-sheath surface of the sleeve itself and are not embedded.

It is advantageous if an electrical contact is connected to the corresponding signal line in an electrically conducting manner. This applies both to signal lines on the inner-sheath surface and to signal lines on the outer sheath surface. If a plurality of signal lines is provided, it may be advantageous if a signal line is interrupted on one side (for example the inside) and continued on the other side (for example the outside). This can be achieved via a conductive connection in a radially extending hole.

For example, the inner-sheath surface of the sleeve may have an electrical contact for a sensor or for another (electronic) component, which is preferably connected in an electrically conducting manner to the corresponding signal lines applied to the inner-sheath surface. This may apply in particular to the magnetic memory readout device.

Furthermore, it is advantageous if the sleeve consists of a plurality of (at least two, preferably three or more) sleeves placed one inside the other. In other words, several sleeves are preferably arranged in several layers. Advantageously, this allows even more functions to be integrated into the sleeve and the installation space is utilized to the maximum.

The sleeve preferably allows signal transmission both from distal to proximal and vice versa, i.e. in the axial direction of the surgical instrument or sleeve, and from the inside to the outside and vice versa, i.e. in the radial direction of the surgical instrument or sleeve.

Overall, multidirectional signal forwarding/transmission is thus provided in the surgical instrument/handpiece (milling handpiece), which is made possible by sleeves with integrated signal lines.

In other words, the invention relates to a handpiece with magnetic tool identification, for example a surgical milling handpiece equipped with automatic tool identification, and the associated tool equipped with a magnetic memory.

In one embodiment, the correct tool type and the corresponding lot number can be read out automatically from the magnetic memory when the tool is put into operation. In particular, the tool can be automatically identified after it has been inserted into the milling handpiece or, respectively, when the foot pedal/hand control is actuated for the first time. The relevant data associated with the identification may be, for example: item number (and thus tool type), lot number, shelf live and the like.

It is possible to indicate to the customer or user of the surgical instrument which product is involved. Various display variants can be provided for this purpose. Additional information can be displayed depending on the tool and handpiece used.

It may also be provided that a controller device, also referred to herein as a control device, of the surgical instrument automatically selects and/or sets the optimum speed suitable for the tool. This can save input work for the customer or user of the surgical instrument.

A preferred embodiment of the invention may comprise a handpiece with an integrated magnetic memory readout device. The handpiece may include a special miniaturized magnetic memory readout device in the distal spacer sleeve thereof.

Another preferred embodiment may be a tool with an integrated magnetic memory. In this preferred embodiment, the tool has an integrated magnetic memory. The shaft of the tool may be made of a non-ferromagnetic steel and may have a recess. The recess is only a few tenths of a millimeter deep.

The shaft can be overmolded with a magnetic-layer carrier made of plastic via an insertion tool. A magnetizable oxide layer (as with magnetic tapes), which is also referred to herein as the magnetic layer, can be applied to this. Finally, a thin layer of protective lacquer may be applied to protect the magnetic layer. The magnetic memory defined herein may include at least the oxide layer or the oxide layer and the magnetic-layer carrier and/or the protective lacquer.

The layer thickness of the magnetic-layer carrier, the magnetic-layer and the protective lacquer may vary. For example, the magnetic layer may be (only) a few hundredths of a millimeter thick (for example, less than 100 μm or less than 50 μm). The protective lacquer layer may, for example, be only a few micrometers thick (for example, less than 10 μm or less than 5 μm).

Furthermore, one embodiment may be provided with a combination of the handpiece as a surgical instrument and the tool. The tool may be inserted into the shaft of the handpiece and locked in place. The magnetic memory readout device integrated in the handpiece may be arranged between the distal ball bearings and the proximal ball bearings of the shaft tip of the handpiece. The magnetic memory of the tool is in close proximity to four Hall sensors, which are the magnetic memory readout device or a part thereof.

The Hall sensors and capacitors, which may be part of the magnetic memory read-out device or may form it together, can fit exactly between a shaft tube of the handheld device and the tool. In particular, six signal lines may be used for signal routing. These are used to connect the supply voltage (Vcc and GND), as well as the four signal outputs of the Hall sensors to the evaluation electronics, also commonly referred to herein as the evaluation unit. The evaluation electronics may be located in the handpiece handle or in the control device, for example, where more space is available. The signal forwarding/signal routing can be carried out by the shaft or sleeve, respectively.

In the preferred embodiment, a tool with a magnetizable/magnetized layer may be used. This can be written or is written on multiple tracks, as with the digital magnetic tapes of earlier tape recorders/data storage devices.

This may be a 7-track magnetic tape with alphanumeric 6-bit code according to DIN 66010, 66011 and 66013. The magnetic tape can be or is digitally written in multiple tracks. The magnetic tape may have a storage density of up to 32 bits per millimeter. The total amount of data that is storable can be influenced by the use of multiple tracks and, of course, by the length of the magnetic tape. This means that very large amounts of data can be stored on a magnetic tape.

A special read head, for example as part of the magnetic memory readout device, can be used to read out the magnetic tapes. Conventional read heads can be too large in size for the very small distal installation space of current milling handpieces to be integrated there. Therefore, a special miniaturized Hall sensor can be used as a read head for reading the magnetized layer on the tool.

The writing of the tools can be carried out directly after their production. Writing/encoding devices of any size can be used for this purpose. Therefore, magnetization with a conventional write head is also possible here.

The tools for a surgical milling handpiece require a fairly small amount of data for identification. In principle, it is sufficient to store the item number and the LOT number on the tool. If these data are stored in a database, it is not even necessary to use an alphanumeric code. Therefore, the data or information about the tool can be stored in a purely binary form. This also has the advantage that the tools are written in coded form and can therefore be protected against counterfeiting.

For example, a 40 bit code may be used. With 40 bits, 1,099,511,628,000 different states can be stored. Without check digit or other security features this is a 13 digit number. Using common conversions, decimal 549,755,813,900 can be stored. A number of tools is significantly less than this number, for example less than 5000 tools or less than 1000 tools or tool types respectively. The lot number may have 8 digits. Thus, 5496 different tools and 99,999,999 different lot numbers can be stored. Thus, a sufficient number of different tools can be represented.

According to an advantageous further development, the tool has to be rotated in the handpiece for reading. The handpiece may have a drive with a rotation speed of approx. 80,000 rpm, which corresponds to 1.333 kHz. The selected miniature Hall sensor may have a readout rate of 20 kHz. At maximum speed of 80,000 rpm, 15 bits per revolution can be detected. The reduction to 10 bits can increase the reliability of the readout. Four tracks may be required for the required 40 bits. With other general conditions, other storage quantities can also be achieved. The tape length is limited in a ring tool with a radius in a range of 2 mm to 3 mm (for example 2 to 2.5 mm), in particular about 2.3 mm or 2.37 mm and thus a circumference of about 7 mm or 7.44 mm circumference. The storage volume can be increased by reducing the reading speed or increasing the number of tracks.

With the tool, the required number of item numbers and/or LOT numbers can be permanently detected during operation at maximum speed.

In particular, one aspect may be writing to and reading from the tool with magnetic memory. The tool may have a magnetizable layer. The dimensions of the unwound layer may be about 8 mm wide and about 7 mm, for example 7.44 mm, long/high. The magnetic-layer may be written with a binary code in four tracks during production. Each track can contain 10 bits. This corresponds to a storage density of 1.34 bit/mm. Each track may contain less than or at most 20 bits (or 15 bits or 10 bits). This is much less than usual tape devices, which can increase the reading reliability. The track width may be 1 mm and the track pitch (center-to-center) may be 2 mm. These values also ensure high reading reliability.

The four Hall sensors may be integrated in the spacer sleeve of the handpiece. Their axial spacing may correspond exactly to the track width or the track spacing. In order to save space, the sensors may be arranged opposite and offset. For example, two Hall sensors each are arranged axially along the sleeve on an inner sheath thereof. Furthermore, the other two Hall sensors may be arranged on an opposite inner sheath of the sleeve parallel to the two respective Hall sensors. Furthermore, the pairs of Hall sensors may also be arranged offset from each other along an inner circumferential direction in a range between 90° and 180°, for example between 100° and 170° or 110° and 160°.

The Hall sensors arranged next to each other in the axial direction along the sleeve can form a pair. The pairs can read tracks 1 and 3 or 2 and 4, respectively, when there are four adjacent tracks.

A (shortest) distance between the magnetic layers arranged on the tool and the respective Hall sensors may be less than 0.1 mm, for example less than 0.05 mm. The distance may be greater than 10 µm. This may apply when the tool or the corresponding part thereof has been received in the milling handpiece and the milling handpiece is ready for operation or in operation.

In order to be able to house the magnetic memory readout device together with the tool in the spacer sleeve, cut-outs, also called recesses herein, may be provided to accommodate the corresponding Hall sensors therein and to increase the inner space for the part of the tool to be received or, respectively, to adjust a distance between Hall sensor(s) and the part of the tool to be received. For example, if the Hall sensors are arranged on an inner wall of the spacer sleeve, there may be no space between the part of the tool to be received and the Hall sensors. The cut-outs in the side wall of the sleeve can remedy this. The conductor tracks can be sunk into an outer side (on the outer sheath) of the sleeve.

The spacer sleeve may also contain the circuitry of the individual components of the magnetic memory readout device on the inside (on the inner sheath) of the sleeve. These can be connected to the signal lines on the outside via small holes.

The Hall sensors used may have a size of about 0.95× 1.4×3.04 mm (housing). This may be a standard SMD component. In addition to the Hall sensor, a capacitor with, for example, a capacitance of 10 nF may be provided. This may have dimensions of 0.5×0.5×1 mm.

In a further embodiment of the invention, integration of the Hall sensors and capacitors may be provided. For mounting, it may be necessary to bend the connection pins of the Hall sensors slightly so that they do not exceed the outer diameter of the spacer sleeve. Due to their small size, the capacitors fit on the inside of the spacer sleeve, for example without cut-outs/recesses. In particular, it may be necessary for the capacitors to be arranged/attached as closely as possible to the respective Hall sensor. This can be realized by positioning them on the inner side. For example, a conduction section between the respective capacitor and Hall sensor may be less than 3 mm (or 2 mm or 1 mm). The capacitor can be connected between Vcc and GND. This allows the supply voltage Vcc to be maintained/smoothed.

In a further embodiment of the invention, a method may be provided, in particular the assembly of the magnetic memory readout device. For the assembly, also called SMT (meaning: surface mounted technique), of the components of the magnetic memory readout device, the SMD technique may be used. The components can be held in position via a fixture and then soldered in the oven or via hot air. For better protection of the electronic components, the inner space of the spacer sleeve may be molded or poured. The adhesive core (placeholder for the tool shaft) can then be removed. This improves the insulation and increases the service life of the components. The tool shaft may be the part of the tool intended to be received in the sleeve with or without the magnetic memory. In particular, the magnetic memory can be inserted or arranged in a recess/indentation of the part of the tool intended to be received in the sleeve in such a way that the magnetic memory is aligned with the tool, i.e. its circumferential surface, or both circumferences are the same.

Variants of the magnetic memory readout device may be:
a reduction to one magnetic track and thus only one Hall sensor,
an extension to 5 to N magnetic tracks (N as a natural number) and several corresponding Hall sensors, and/or
a use of a special 'miniature sound head' instead of a Hall sensor.

The following four variants of the tool or of the magnetic memory may be provided:
Variant 1: tool with slide-on magnetic memory. For easier assembly, it may be advantageous to configure the magnetic memory so that it can be slid on.
Variant 2: tool with wire-magnetic memory. In order to achieve a stronger magnetization, a magnetized wire may be used. Each wire ring may correspond to a track. The magnetized bits may be distributed along the wire ring, for example evenly spaced.
Variant 3: tool with miniature magnets in cylindrical form. An even stronger magnetization can be made possible with individual magnetized wire pieces or with small permanent magnets. These are either pressed or glued into place. In the case of wire pieces, all holes may be filled. Magnetization then takes place via a writing device. The writing device may be able to adapt/change the magnetization according to the information about the tool. With permanent magnets, only the holes are filled according to the 'one bits'. The remaining holes 'zero bits' remain empty or are filled with the protective lacquer.
Variant 4: tool with miniature magnets in spherical shape. Spherical permanent magnets are easier to mount since no orienting is required. The specific orientation of the individual magnetic poles can be achieved by externally attached magnets (permanent/electrical) with a mounting device. The fixation is done via adhesives. As with the variant mentioned above, only the 'one bits' are filled. Thus, a bit pattern can be created along the circumference via magnetization.

It is clear to the person skilled in the art that the explanations stated herein are/may be implemented using hardware circuits, software means, or a combination thereof. The software means may be related to programmed microprocessors or a general computer, an ASIC (Application Specific Integrated Circuit) and/or DSPs (Digital Signal Processors).

For example, the processing unit, evaluation unit, motor unit, control device, writing device, magnetic memory readout device, and/or surgical instrument itself may be partially implemented as a computer, a logic circuit, an FPGA (Field Programmable Gate Array), a processor (for example comprising a microprocessor, a microcontroller ($\mu$C) or a vector processor)/core (main memory, may be integrated in the processor or used by the processor)/CPU (Central Processing Unit; wherein multiple processor cores are possible), an FPU (Floating Point Unit), an NPU (Numeric Processing Unit), an ALU (Arithmetic Logical Unit), a coprocessor (additional microprocessor to support a main processor (CPU)), a GPGPU (General Purpose Computation on Graphics Processing Unit): a parallel computer (for simultaneous execution of computational operations on several main processors and/or graphics processors, among others) or a DSP.

Although some of the aspects described above apply to the surgical instrument, these aspects may also apply to the tool. Likewise, the aspects described above in relation to the tool may apply in a corresponding manner to the surgical instrument.

If it is said that a component is "connected" or "in connection" with another component, this can mean that it is directly connected with it; however, it should be noted that a further component may lie in between. If, on the other hand, it is said that a component is "directly connected" to another component, this is to be understood to mean that there are no other components in between.

BRIEF DESCRIPTION OF THE DRAWING FIGURES

The invention is explained below with the aid of drawings, of which:

FIG. 1*a* shows a schematic representation of a surgical instrument;

FIG. 1*b* shows a schematic representation of a tool in a first perspective;

FIG. 1*c* shows a schematic representation of a tool in a second perspective;

FIG. 2*a* shows a schematic representation of a first variant of a user interface with indications;

FIG. 2*b* shows a schematic representation of a second variant of a user interface;

FIG. 2*c* shows a schematic representation of a third variant of a user interface;

FIG. 3 shows a schematic representation of a sleeve of a surgical instrument;

FIG. 4*a* shows a schematic representation of a tool with magnetic memory in a first perspective;

FIG. 4*b* shows a schematic representation of a tool with magnetic memory in a second perspective;

FIG. 4*c* shows a schematic representation of a tool with magnetic memory in a third perspective;

FIG. 5*a* shows a schematic representation of a surgical instrument with tool in longitudinal section;

FIG. 5*b* shows a schematic representation of a sleeve of a surgical instrument with tool in longitudinal section;

FIG. 5c shows a schematic representation of a part of a sleeve of a surgical instrument with tool in longitudinal section;

FIG. 7 shows a schematic representation of a magnetic tape;

FIG. 8 shows a schematic representation of a table of magnetic memories with typical data;

FIG. 10a shows a schematic representation of a sleeve with recesses and signal lines in a first perspective;

FIG. 10b shows a schematic representation of a sleeve with recesses and signal lines in a second perspective;

FIG. 17a shows a schematic representation of a fourth variant of a tool with magnetic memory in a first perspective;

FIG. 17b shows a schematic representation of a fourth variant of a tool with magnetic memory in a second perspective; and FIG. 17c shows a schematic representation of a fourth variant of a tool with magnetic memory in a third perspective.

DETAILED DESCRIPTION

Figure 3:
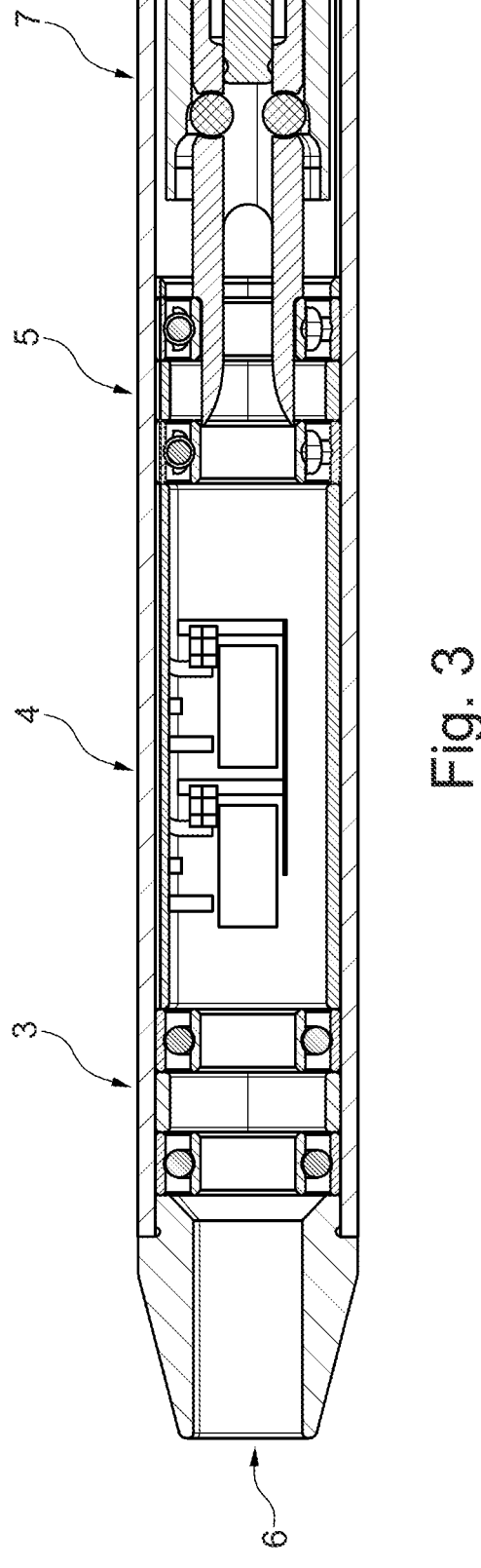

The figures are of a schematic nature only and are intended solely for the purpose of understanding the invention. Identical elements are provided with the same reference signs. The features of the individual embodiments can be interchanged.

In addition, spatially relative terms, such as "located below," "below," "lower," "located above," "upper," "on the left," "left," "on the right," "right," and the like, may be used herein to simply describe the relationship of an element or structure to one or more other elements or structures shown in the figures. The spatially relative terms are intended to include other orientations of the structural element in use or operation in addition to the orientation shown in the figures. The structural element may be oriented differently (rotated 90 degrees or in a different orientation), and the spatially relative descriptors used herein may likewise be interpreted accordingly.

The surgical instrument and the tool are now described using embodiments.

The basic principle of the present invention is based on the Hall effect occurring in a current-carrying electrical conductor (provided by a supply voltage Vcc and ground GND) which is in a magnetic field, wherein an electric field is established which is perpendicular to the direction of the current and to the magnetic field and which compensates for the Lorentz force acting on the electrons.

For this purpose, a magnetic memory readout device is provided in a sleeve 4 of a surgical instrument 1. At the same time, a tool 2 is provided which has a magnetic memory layer 8 forming a circumference of the tool 2 or respectively arranged around the tool shaft 16 which rotates during actuation of the surgical instrument 1 by engagement with a motor unit of the surgical instrument 1. The magnetic-memory layer 8 comprises information about type/kind of tool 2 in the form of magnetization, similar to a tape. When the magnetic-memory layer 8 is rotated in accordance with the rotation of the tool 2, the magnetic-memory layer 8 is moved past the magnetic memory readout device, for example in the form of Hall sensors 12. Based on the Hall effect, a voltage in the form of a (voltage) signal is induced in the magnetic memory readout device due to the variable electric or magnetic field caused by the rotation of the magnetic memory layer 8. This process may also be referred to as readout herein. This voltage signal is then forwarded via signal lines 13 to an evaluation unit, which processes the information on the tool 2 underlying the voltage signal and can finally make it accessible to the user of the surgical instrument 1 via a user interface.

FIG. 1a shows a schematic representation of a surgical instrument 1 in the form of a milling handpiece for receiving a tool 2 shown in two different perspectives in FIGS. 1b and 1c. In particular, the present disclosure may serve the purpose of identifying which type/kind of tool 2 is involved when the milling handpiece of an associated foot pedal (not shown) is actuated.

The surgical instrument 1 as well as the tool 2 each have three essential sections. The surgical instrument 1 has a connecting portion 1.1 for connecting the handpiece to the corresponding electronic devices such as control device and user interface, a motor unit 1.2 for providing the drive for the corresponding tool, which is connected to the tool-interface unit 1.3, which also includes the sleeve used herein, in particular spacer sleeve.

The tool 2 has a handle portion 2.1, a shaft portion 2.2 and at least one working end/effector 2.3. In particular, the handle portion 2.1 of the tool 2 can be configured to interact with the tool interface unit 1.3 or the spacer sleeve, respectively, in such a way that these two elements are form-fittingly or force-fittingly connected.

Further details and aspects are mentioned in connection with the embodiments described above or below. The embodiment shown in FIGS. 1*a*, 1*b*, and 1*c* may have one or more optional additional features corresponding to one or more aspects mentioned in connection with the proposed concept or embodiments described below with respect to FIGS. 2*a*-17*c*.

FIGS. 2*a*, 2*b* and 2*c* show different variants of a user interface which serve to provide the user with the relevant information about the tool 2 in use. These user interfaces may be in wireless or wired communication with the surgical instrument 1 or may be connected to it, respectively.

In particular, this provides a tool identification which is passed on to peripheral devices such as the user interface via data transmission and displays selected data to the end customer, i.e. the user, relating to the information read out by the magnetic memory readout device. At the same time, other data can be logged and further processed. These data may already be present or updated on a data carrier assigned to the user interface. The data and information about the tool 2 referred to herein may be in particular an item number, a lot number, a batch number, a shelf live, an expiration date or maximum use date, material, dimensions and geometries, intended use, previous uses and duration of use, inventory levels, etc.

Furthermore, the information read out can be displayed to the user of the tool 2. Alternatively or additionally, data of the tool 2 can be stored from the read-out information and/or forwarded to the provider of the tool 2. The aforementioned processes preferably run automatically, so that the data can in particular be automatically displayed and/or forwarded and/or stored in a database.

A user can thus, in the context of using a particular medical engineering tool such as the surgical instrument 1, safely, easily, quickly and in particular automatically obtain information about which tool 2 he is currently using or intends to use and/or is connected to the surgical instrument 1, without having to look at a label or package. In particular, a user can automatically and easily identify whether the surgical instrument 1 being used is suitable or unsuitable for a particular application by pressing it once.

Furthermore, the user can easily determine which stocks of the relevant tool 2 are still in his warehouse (or consignment warehouse) without having to carry out an inventory.

In summary, automatic identification of the tool 2 used in each case, in particular of the tool 2 used in each case with the surgical instrument 1, can be made possible. In addition, particularly simple and largely error-proof maintenance and/or transmission of data associated with the tool 2 can be made possible.

Thus, the surgical tool 1 provided herein provides direct, automated tool identification for both a user and a provider (supply chain management (SCM), service, failure analysis). It also provides transmission of any number of other data to the user and/or the provider. It can also be used to record product-related data automatically and promptly in a patient file.

Further details and aspects are mentioned in connection with the embodiments described above or below. The embodiment shown in FIGS. 2*a*, 2*b*, and 2*c* may have one or more optional additional features corresponding to one or more aspects mentioned in connection with the proposed concept or one or more embodiments described above (e.g., FIG. 1) or below (e.g., FIGS. 3-17*c*).

FIG. 3 shows a schematic representation of a sleeve 4 of a surgical instrument 1. As shown in FIG. 3, the sleeve 4 has a receiving opening 6 for the tool 2, which can be pushed into the sleeve 4 from the left. The tool 2 can be pushed into the sleeve 4 up to a fixing device 7. The tool 2 or the handle portion 2.1 can be detachably connected to the sleeve at the fixing device 7. In this respect, the fixing device 7 forms at least part of the tool interface unit 1.3 or is this. To the left of the fixing device 7 is a ball bearing 5. Still further to the left, the magnetic memory read-out device, which is crucial for the present invention, is arranged in the sleeve. Further to the left is another ball bearing 3. The ball bearings 3 and 5 can also be rolling bearings in general. The purpose of the two ball bearings on the left 3 and right 5 next to the section of the sleeve 4 with the magnetic memory readout device is to fix the part of the tool 2 acting as an axis or shaft, respectively, received in the sleeve 4. The two ball bearings on the left 3 and right 5 can absorb radial and/or axial forces and at the same time enable the rotation of the axis/shaft of the part of the tool 2 received in the sleeve 4. In particular, the magnetic memory readout device is miniaturized so that the part of the tool 2 intended to be received in the sleeve 2 is spaced apart.

Further details and aspects are mentioned in connection with the embodiments described above or below. The embodiment shown in FIG. 3 may have one or more optional additional features corresponding to one or more aspects mentioned in connection with the proposed concept or one or more embodiments described above (e.g., FIGS. 1-2*c*) or below (e.g., FIGS. 4*a*-17*c*).

FIGS. 4*a*, 4*b* and 4*c* show various views of a tool 2 with magnetic memory 8. The magnetic memory 8 surrounds the tool 2 shown in FIGS. 4*a*, 4*b* and 4*c* in such a way that a surface of the tool shaft transitions continuously to a surface of the magnetic memory 8. For this purpose, an indentation with a predetermined width along the circumference may be provided into which the magnetic memory 8 can be fitted. In particular, this indentation may be greater than 0.1 mm and less than 0.4 mm.

The magnetic memory 8 may optionally be configured as follows.

First, a magnetic layer carrier 11 may be applied to the indentation. An oxide layer 10 is then applied to this magnetic layer carrier 11 as a magnetic layer. Finally, a protective lacquer 9 is applied to protect the magnetic layer 10. The layer thicknesses of these three layers 9, 10, 11 can vary. The total layer thickness of all three layers can correspond to a depth of indentation in order to provide an essentially smooth surface of the tool 2.

The functionality of the magnetic memory is independent of the material of the tool. The shaft of the tool 2 or the tool 2 itself may be made of ferromagnetic— and non-ferromagnetic—material, respectively.

Further details and aspects are mentioned in connection with the embodiments described above or below. The embodiment shown in FIGS. 4*a*, 4*b*, and 4*c* may have one or more optional additional features corresponding to one or more aspects mentioned in connection with the proposed concept or one or more embodiments described above (e.g., FIGS. 1-3) or below (e.g., FIGS. 5*a*-17*c*).

FIGS. 5*a*, 5*b* and 5*c* show a surgical instrument 1 with a tool 2 received therein. In particular, FIG. 5*a* shows a schematic representation of a surgical instrument 1 with tool 2 in longitudinal section. FIG. 5*b* shows a schematic representation of a sleeve 4 of a surgical instrument 1 with tool 2 in longitudinal section. FIG. 5*c* shows a schematic representation of a part of a sleeve 4 of a surgical instrument 1 with received tool 2 in longitudinal section.

Specifically, when operating the surgical instrument 1 with inserted tool 2, the magnetic memory 8 can interact with the magnetic memory readout device such that information can be output via the magnetic memory readout device to the user interfaces shown in FIGS. 2a, 2b and 2c. In particular, the magnetic memory readout device has a plurality of Hall sensors 12, as shown in FIG. 5c. For example, the Hall sensors 12 may form at least a part of, or may be referred to as, the magnetic memory readout device. The Hall sensors 12 are offset from each other such that they can read out a different track located on the magnetic memory 8 of the tool 2. For this purpose, the Hall sensors 12 only require a supply voltage Vcc. This supply voltage Vcc can be smoothed by upstream capacitors 15. The capacitors 15 may also be part of the magnetic memory readout device or may form it together with the Hall sensors 12.

When the tool shaft rotates, the magnetic memory 8 also rotates in the direction of rotation. This rotation can be triggered via a foot pedal, which is directly or indirectly connected to the surgical instrument. This creates a time-varying magnetic field corresponding to a magnetization on the magnetic memory 8. These magnetic field changes contain the information about the tool 2 and can be recorded or read out via the Hall sensors 12 in the form of voltage changes. These voltage changes can also be understood as voltage signals, which contain the information about the tool 2 in the form of voltage states. A signal output of the Hall sensors 12 can be connected to a respective signal line 13 of the sleeve 4 in such a way that a signal can be forwarded to a processing unit or evaluation unit external or internal to the surgical instrument 1.

Thereupon, one of the user interfaces as shown in FIGS. 2a, 2b and 2c can be fed with the necessary information about the tool 2 and can thus be communicated to the user of the surgical instrument 1.

Further details and aspects are mentioned in connection with the embodiments described above or below. The embodiment shown in FIGS. 5a, 5b, and 5c may include one or more optional additional features corresponding to one or more aspects mentioned in connection with the proposed concept or one or more embodiments described above (e.g., FIGS. 1-4c) or below (e.g., FIGS. 6-17c).

Figure 6:
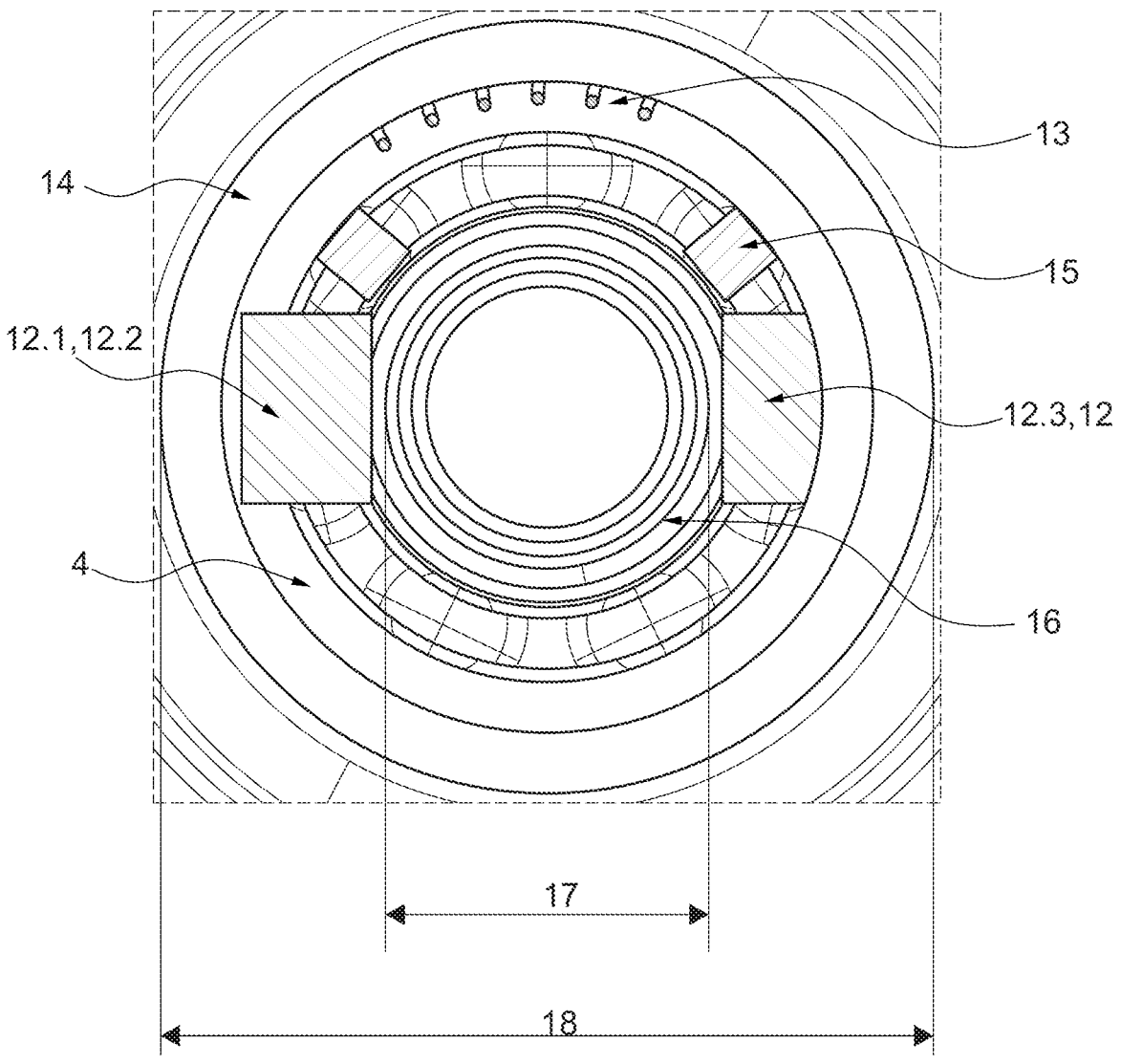
FIG. 6 shows is a schematic representation of a cross-section through a surgical instrument with the tool in place.

FIG. 6 shows a schematic representation of a cross-section through a surgical instrument 1 with received tool 2. The surgical instrument 1 has a shaft tube 14 surrounding the sleeve 4. The signal lines 13 are housed or recessed in the sleeve 4 or in the shaft tube 14 with a first diameter 18. The first diameter 18 may be in a range of 5 to 6 mm, in particular about 5.6 mm. In order to prevent the signal lines 13 from being short-circuited, the sleeve 4 or the shaft tube 14 respectively has to be made of a non-conductive material, for example ceramic. In order for the signal lines 13 to reach the inner space or the inner sheath of the sleeve 4, bores (not shown) are provided which guide the signal lines 13 on to the inner sheath of the sleeve 4. The signal lines 13 applied to the inside or inner sheath are connected to the structural elements of the magnetic memory read-out device, in particular the capacitors 15 and the Hall sensors 12. This connection may be a solder connection on the inner sheath of the sleeve 4. In the example of FIG. 6, two Hall sensors 12.1 and 12.2 are arranged on the left inner side of sleeve 4 and two Hall sensors 12.3 and 12.4 on the right inner side of sleeve 4. The capacitors 15 are in direct electrical connection with the Hall sensors 12 and smooth the input signal of the supply voltage Vcc.

The tool shaft 16 of the tool 2 is arranged in the space between the structural elements of the magnetic memory readout device. FIG. 6 thus represents the case during operation or shortly before operation. As can be seen in FIG.

6, the Hall sensors 12 are recessed in the sleeve wall so that the tool shaft 16 fits into the sleeve 4. A diameter of the tool shaft 16 may be in a range of 2 to 3 mm, in particular about 2.37 mm. The Hall sensors 12 may be arranged in such a way that they do not protrude beyond an outer diameter of the sleeve 4.

The individual signal lines 13 may have different functions and are not limited to the number of six as shown in FIG. 6. At least one signal line 13 is provided for the supply voltage Vcc. In case of increased current demand, several signal lines 13 may be provided for the supply voltage Vcc. In particular, this can also define the ground connection GND. In the case of a supply voltage Vcc, one ground connection GND is also sufficient. In the case of several signal lines 13 as supply voltage Vcc, the requirement for signal lines 13 for ground GND may also increase. FIG. 6 also shows four signal lines 13 as communication lines for each of the Hall sensors 12. Thus, for example, at least three signal lines 13 may be present in the sleeve 4 to ensure the function of the Hall sensor 12, in particular power supply and communication. If further Hall sensors 12 are present, the number of signal lines 13 may be increased proportionally.

Further details and aspects are mentioned in connection with the embodiments described above or below. The embodiment shown in FIG. 6 may have one or more optional additional features corresponding to one or more aspects mentioned in connection with the proposed concept or one or more embodiments described above (e.g., FIGS. 1-5c) or below (e.g., FIGS. 7-17c).

FIG. 7 shows a schematic representation of a magnetic tape. In this example, it is a 7-track magnetic tape with alphanumeric 6-bit code, which has a parity bit 19 for checking, two zone bits 20 and four numeric bits 21. As an example, such a magnetic tape can be attached in bit alignment according to the 6-bit code along the circumference to the tool 2 to function as a magnetic memory 8. For this purpose, for example, DIN standards can be used, such as DIN 66010, 66011, 66013. FIG. 8 shows in this respect a schematic representation of a table of magnetic memories with typical data to which reference is made herein only by way of example.

Further details and aspects are mentioned in connection with the embodiments described above or below. The embodiment shown in FIGS. 7 and 8 may include one or more optional additional features corresponding to one or more aspects mentioned in connection with the proposed concept or one or more embodiments described above (e.g., FIGS. 1-6) or below (e.g., FIGS. 9-17c).

Figure 9:
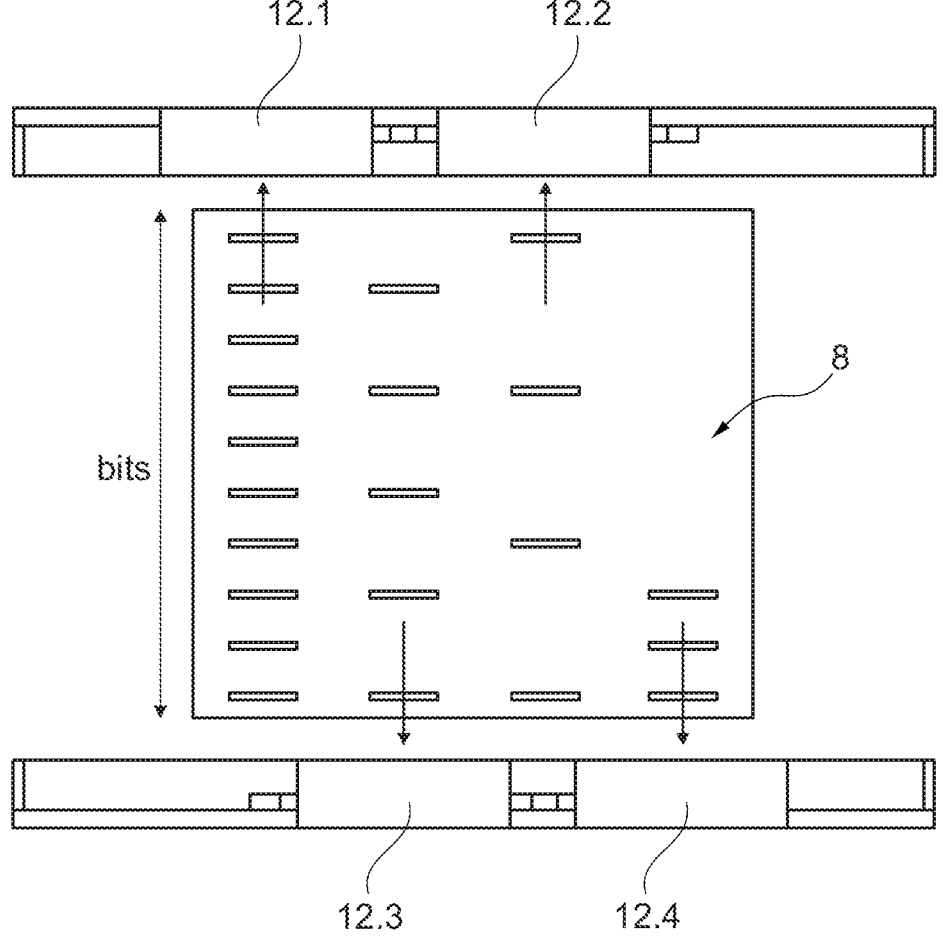
FIG. 9 shows a schematic representation of a magnetic memory interacting with magnetometers within the sleeve of a surgical instrument.
Figure 11:
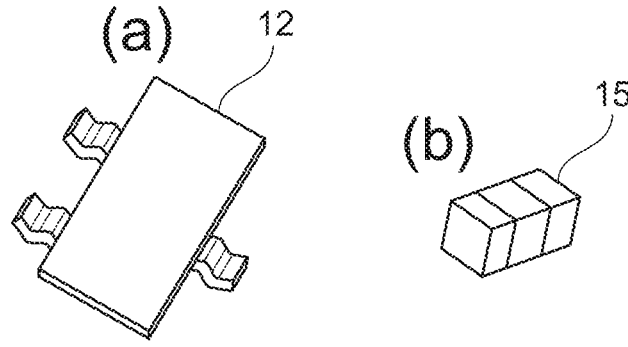
FIG. 11a shows a schematic representation of a Hall sensor as SMD component.
FIG. 11b shows a schematic representation of a capacitor as SMD component.

FIG. 9 shows a schematic representation of a magnetic memory 8 in interaction with magnetometers in the form of Hall sensors 12.1, 12.2, 12.3, 12.4 within the sleeve 4 of a surgical instrument 1. The magnetic memory 8 is shown here rolled out flat as an example. Specifically, the number of bits is indicated from bottom to top (i.e., in use along the circumference of the tool 2). In FIG. 9, one track for each of the Hall sensors 12 is arranged so that it rotates directly past the corresponding Hall sensor 12 during operation. The individual tracks are shown exemplarily via arrows. Each track contains 10 bits in this example.

The adjacent tracks (from left to right) have a center-to-center distance that corresponds to the center-to-center distance of the (opposite) Hall sensors 12 provided for these tracks. The center-to-center distance may be at least twice the track width or correspond to at least twice the track width, respectively. The center-to-center spacing of Hall sensors 12 adjacent to each other in the axial direction may correspond to at least four times a track width. The number of tracks also corresponds to the number of Hall sensors 12 used. Thus, one of the Hall sensors 12 may be provided for exactly one of the tracks on the magnetic memory 8.

For space reasons, adjacent tracks are not read by adjacent Hall sensors 12.1, 12.2 or Hall sensors 12.3, 12.4, but by opposite Hall sensors 12.1, 12.3 or 12.2, 12.4. The Hall sensors 12 do not necessarily have to be directly opposite each other on the inner-sheath surface of the sleeve 4, but they do have to be arranged offset from each other along the inner circumferential direction of the sleeve 4. Thus, Hall sensors 12 that are not adjacent in the axial direction can be arranged offset in the inner circumferential direction of the sleeve 4. For example, as shown in FIG. 9, pairs of Hall sensors (12.1, 12.2; 12.3, 12.4) can be arranged offset from each other in the inner circumferential direction of the sleeve 4. The pairs may be arranged, for example, directly opposite each other on an inner-sheath surface of the sleeve 4. In this case, the Hall sensors 12 of the respective pairs of Hall sensors (12.1, 12.2; 12.3, 12.4) may be arranged one behind the other or side by side, respectively, in the axial direction of the sleeve 4.

Further details and aspects are mentioned in connection with the embodiments described above or below. The embodiment shown in FIG. 9 may include one or more optional additional features corresponding to one or more aspects mentioned in connection with the proposed concept or one or more embodiments described above (e.g., FIGS. 1-8) or below (e.g., FIGS. 10a-17c).

FIG. 10a shows a schematic representation of a sleeve 4 with recesses 22 and signal lines 13 in a first perspective. The same sleeve 4 is shown in a different perspective in FIG. 10b. The recesses 22 are holes in the sleeve 4 or, respectively, in the side wall of the sleeve 4. Holes are therefore provided as recesses 22 so that the Hall sensors 12 can be easily attached. The holes are configured to be large enough for a main body of the respective Hall sensors to fit into them. Pins for connecting the Hall sensor 12 to the signal lines 13 are located directly next to or on the holes. These pins are located in further recesses 23 on an outer sheath of the sleeve 4. These are not configured as holes. The recesses 23 are used for electrical connection to the signal lines 13. This also means a mechanical connection, for example in the form of a solder, which connects the respective Hall sensors 12 electrically and mechanically to the pins in the recesses 23.

The signal lines 13 lead from the pins of the recesses 23 via bores to an inner-sheath surface of the sleeve 4. There, the signal lines 13 run in the axial direction of the sleeve 4 along the inner-sheath surface and in the inner circumferential direction of the sleeve 4. Furthermore, the signal lines 13 lead via further bores to the passage-shaped signal lines 13, as shown in FIG. 10b. These only run along an axial direction of the sleeve 4, so that communication of the surgical instrument 1 with a peripheral device, for example the evaluation unit or the user interface, is provided via the sleeve 4.

Further details and aspects are mentioned in connection with the embodiments described above or below. The embodiment shown in FIGS. 10a and 10b may include one or more optional additional features corresponding to one or more aspects mentioned in connection with the proposed concept or one or more embodiments described above (e.g., FIGS. 1-9) or below (e.g., FIGS. 11a-17c).

FIG. 11a shows a schematic diagram of a Hall sensor 12 as an SMD component. The Hall sensor 12 has three terminals, a terminal for the power supply Vcc, a terminal for the ground GND and a voltage-signal output. These may be optionally provided on the Hall sensor 12 or may be preset. Via the terminals, the Hall sensor 12 can be engaged with the pins of the recess 23. The terminals can be bent accordingly so that a force fit with the recesses 23 or with the pins of the recesses 23 is created. Solder can be additionally applied here to ensure the electrical and mechanical connection. A capacitor 15 is used in conjunction with the Hall sensor 12. This is shown in FIG. 11b as an SMD component. The capacitor 15 has exactly two terminals and has no preferred direction. Thus, the capacitor 15 can be attached or soldered to signal lines 23 running along the inner-sheath surface. The frame size, for example the height, of the capacitor 15 is smaller than the frame size of the Hall sensor 12, for example at least smaller than a wall thickness of the sleeve 4.

Figure 12:
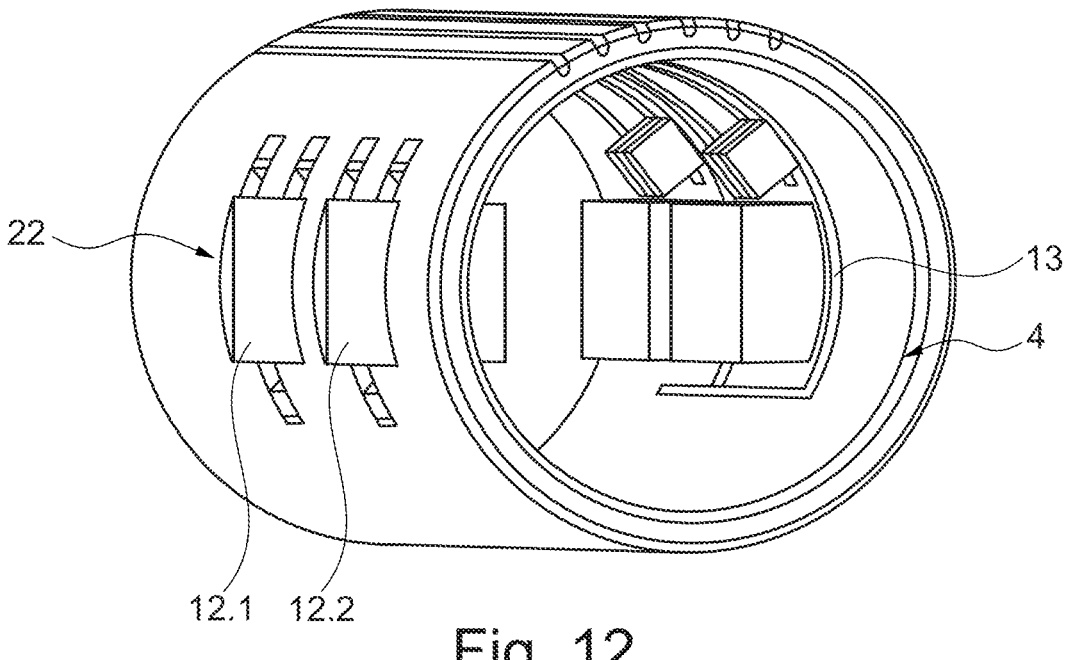
FIG. 12 shows a schematic representation of a sleeve with Hall sensors and capacitors.
Figure 13:
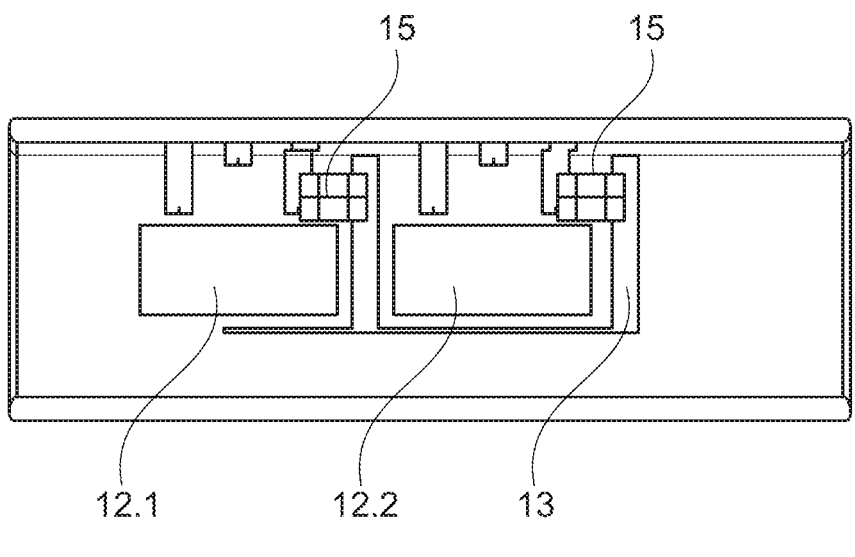
FIG. 13 shows a schematic view of a longitudinal section of a sleeve with Hall sensors and capacitors.

For the sake of completeness, FIG. 12 shows a sleeve 4 with Hall sensors 12 and capacitors 15 attached to it and the associated signal lines 13. The sleeve is also shown in longitudinal section with structural elements 12 and 15 in FIG. 13. In order to keep the structural elements 12, 15 in their position, soldering can be carried out in an oven or via hot air. On the other hand, the inner space of the sleeve 4 may be cast with a non-conductive material. A dummy tool may be used as a spacer for the actual tool 2 so that the space for it remains free during casting. This can increase the service life of the structural elements 12, 15. The dummy tool may have a larger circumference than the tool shaft of the tool 2. This difference may be in the range from 2% to 25%, preferably in the range from 10% to 20%.

Further details and aspects are mentioned in connection with the embodiments described above or below. The embodiment shown in FIGS. 11a, 11b, 12, and 13 may include one or more optional additional features corresponding to one or more aspects mentioned in connection with the proposed concept or one or more embodiments described above (e.g., FIGS. 1-12) or below (e.g., FIGS. 14-17c).

FIGS. 14 to 17c show various embodiments of the tool 2 with magnetic memory 8.

Figure 14:
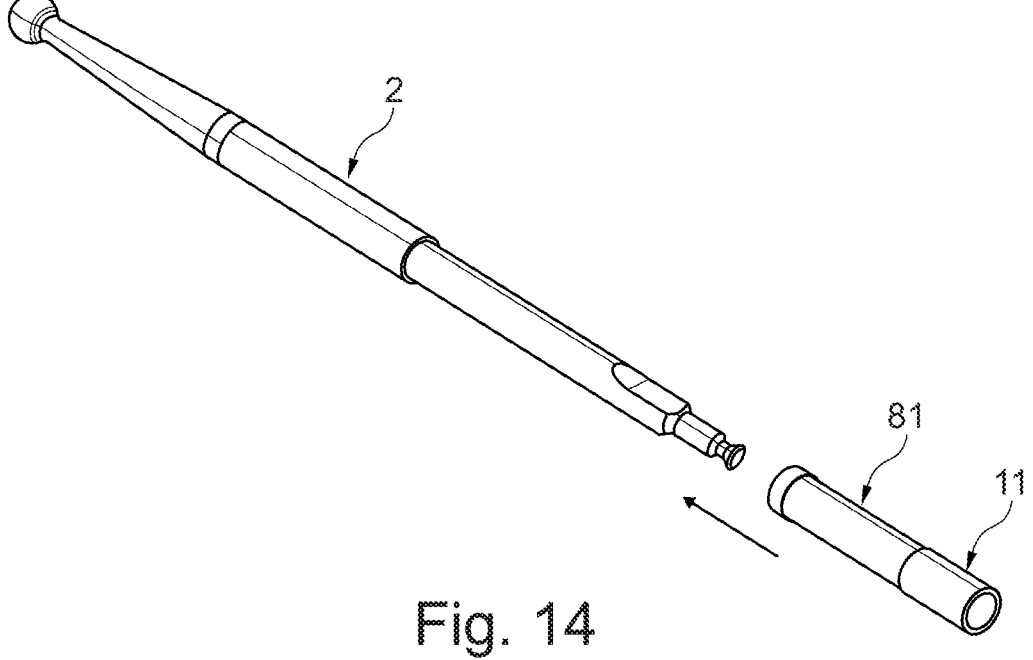
FIG. 14 shows a schematic representation of a first variant of a tool with magnetic memory.
Figure 15:
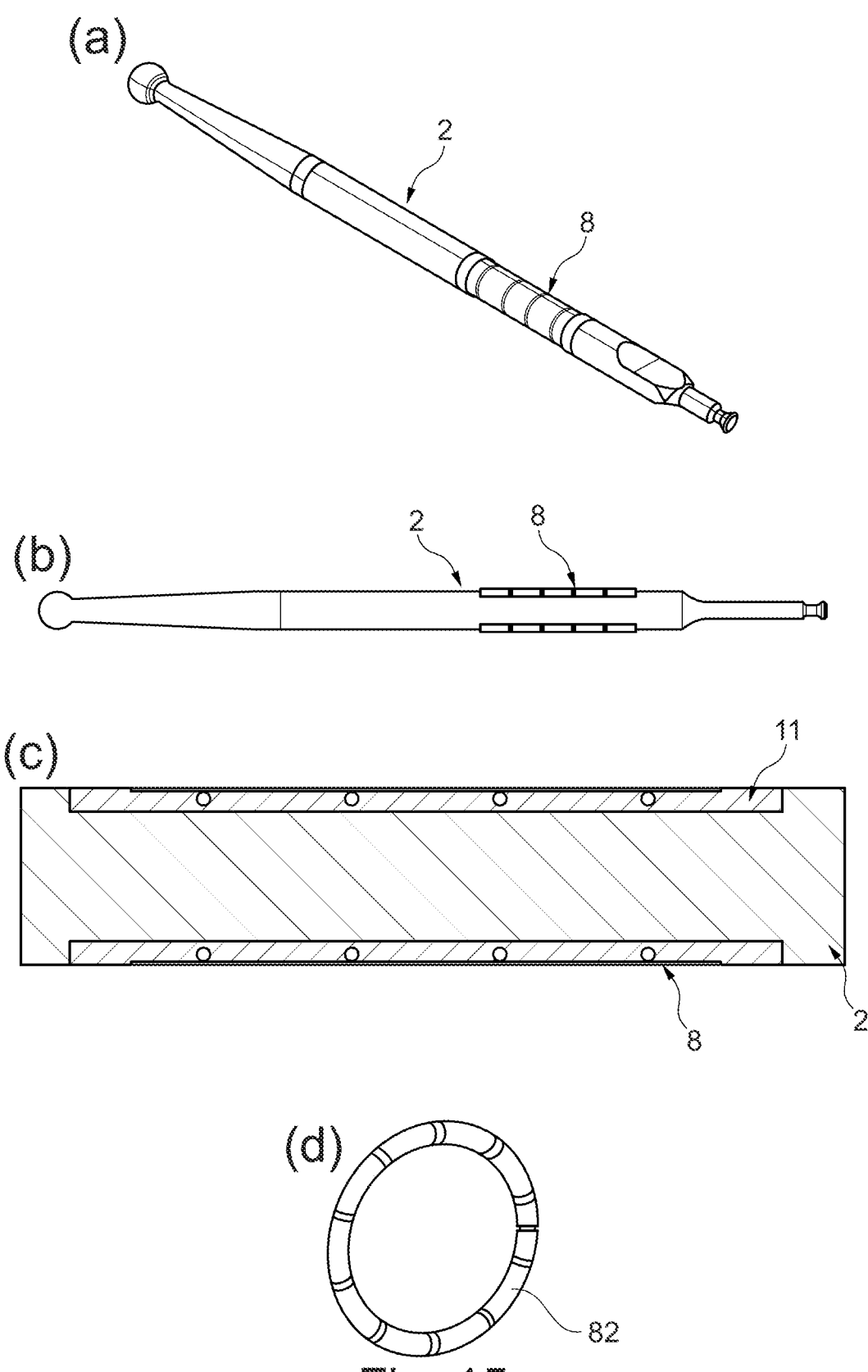
FIG. 15a shows a schematic representation of a second variant of a tool with magnetic memory in a first perspective.
FIG. 15b shows a schematic representation of a second variant of a tool with magnetic memory in a second perspective.
FIG. 15c shows a schematic representation of a second variant of a tool with magnetic memory in a third perspective.
FIG. 15d shows a schematic representation of a second variant of a tool with magnetic memory in a fourth perspective.
Figure 16:
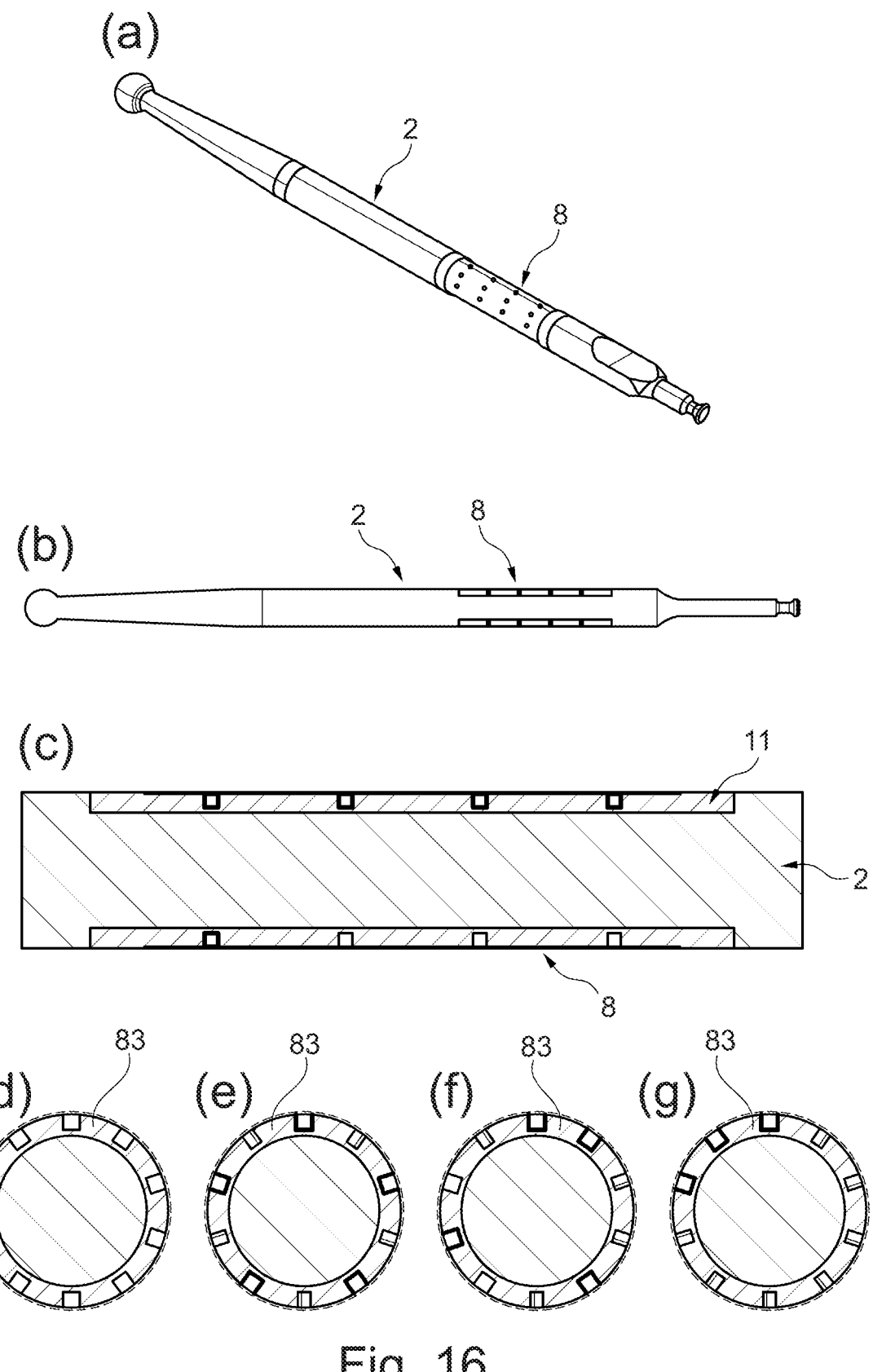
FIG. 16a shows a schematic representation of a third variant of a tool with magnetic memory in a first perspective.
FIG. 16b shows a schematic representation of a third variant of a tool with magnetic memory in a second perspective.
FIG. 16c shows a schematic representation of a third variant of a tool with magnetic memory in a third perspective.
FIG. 16d shows a schematic representation of a third variant of a tool with magnetic memory in a fourth perspective.
FIG. 16e shows a schematic representation of a third variant of a tool with magnetic memory in a fourth perspective.
FIG. 16f shows a schematic representation of a third variant of a tool with magnetic memory in a fourth perspective.
FIG. 16g shows a schematic representation of a third variant of a tool with magnetic memory in a fourth perspective.

FIG. 14 shows a schematic representation of a first variant of a tool 2 with magnetic memory 8. Here, the magnetic memory 8 can be detachably connected to the tool 2 in the form of a magnetic memory sleeve 81. Thus, the tool 2 and the magnetic memory 8 may be supplied separately. The magnetic memory 8 can be regarded as part of the tool 2. The tool 2 may be adapted in such a way that a part of the tool 2 intended for the magnetic memory 8 has a circumference which is correspondingly smaller than the thickness of the magnetic memory 8 or its sheath thickness. Thus, an inner sheath diameter of the magnetic memory 8 may correspond approximately to a diameter of the part of the tool 2 provided for the magnetic memory 8.

Further details and aspects are mentioned in connection with the embodiments described above or below. The embodiment shown in FIG. 14 may include one or more optional additional features corresponding to one or more aspects mentioned in connection with the proposed concept or one or more embodiments described above (e.g., FIGS. 1-13) or below (e.g., FIGS. 15a-17c).

FIGS. 15a, 15b and 15c show various views of a second variant of a tool 2 with magnetic memory 8. FIG. 15d shows a schematic representation of the magnetic memory 8 as it is provided in the second variant. In particular, several magnetized wire rings 82 may be arranged side by side at a predetermined distance in the axial direction of the tool 2. The spacing may correspond to the center-to-center spacing defined above. In particular, the wire rings 82 may be molded or overmolded in a plastic 11 that at least partially covers the wire rings. In particular, the plastic 11 may be molded in a recess in such a way that the plastic 11 is flush with the tool 2.

Further details and aspects are mentioned in connection with the embodiments described above or below. The embodiment shown in FIGS. 15a, 15b, 15c, and 15d may include one or more optional additional features corresponding to one or more aspects mentioned in connection with the proposed concept or one or more embodiments described above (e.g., FIGS. 1-14) or below (e.g., FIGS. 16a-17c).

FIGS. 16a to 16g show schematic representations of a third variant of a tool 2 with magnetic memory 8. In this case, the magnetic memory 8 is provided in the form of small permanent magnets as a permanent magnet assembly 83 or may comprise writable wire pieces. The permanent magnets may be arranged differently along a circumferential direction of the magnetic memory 8, see FIGS. 16d to 16g, for example included or not included (according to the bit pattern provided for the information about the tool 2). In the case of the pieces of wire, they may be written or not written, that is, magnetized or not magnetized. In this way, the information about the tool can be integrated into the magnetic memory 8.

Further details and aspects are mentioned in connection with the embodiments described above or below. The embodiment shown in FIGS. 16a-16g may include one or more optional additional features corresponding to one or more aspects mentioned in connection with the proposed concept or one or more embodiments described above (e.g., FIGS. 1-15d) or below (e.g., FIGS. 17a-17c).

FIGS. 17a, 17b and 17c show schematic representations of a fourth variant of a tool 2 with magnetic memory 8. In particular, the magnetic memory 8 has an assembly of spherical magnets 84. The magnets may be attached at predetermined positions around the tool 2 or on the tool 2, respectively. The bit pattern is obtained by writing via a writing device, which magnetizes the spherical magnets 84 according to the bit pattern intended for the information about the tool 2.

The invention claimed is:

1. A surgical instrument comprising:
a connecting portion; and
a spacer sleeve,
the spacer sleeve comprising:
    a coupling portion in a proximal region of the spacer sleeve for mechanical coupling to a surgical handpiece for configuring a surgical instrument;
    a tool receptacle in a distal region of the spacer sleeve; one or more signal lines;
    a drive power transmission element mounted in the spacer sleeve for transmitting a drive power from a drive to a tool inserted in the tool receptacle; and
    a readout device arranged in the spacer sleeve in the distal region of the spacer sleeve,
the readout device being connected to the one or more signal lines,
the one or more signal lines being connected in the proximal region of the spacer sleeve to one or more line couplings configured to be connected to an evaluation unit when the spacer sleeve is coupled to the surgical handpiece,
the readout device comprising at least one magnetometer, and
the spacer sleeve comprising at least one recess in a side wall in which a part of the at least one magnetometer is located.

2. The surgical instrument according to claim 1, wherein the at least one magnetometer is a Hall sensor comprising a surface-mounted SMD component.

3. The surgical instrument according to claim 1, wherein a readout occurs when the surgical instrument is actuated.

4. The surgical instrument according to claim 1, wherein the one or more signal lines extend axially along the spacer sleeve, and wherein the readout device is configured to read out information contained in a magnetic memory about the tool based on a magnetic memory surrounding a periphery of a part of the tool and to transmit said information via the one or more signal lines to an evaluation unit.

5. The surgical instrument according to claim 1, wherein the readout device is located within a space defined by an outer sheath of the spacer sleeve.

6. The surgical instrument according to claim 1, wherein the one or more signal lines are formed by passages coated with a conducting material.

7. The surgical instrument according to claim 1, wherein the readout device is mounted between bearings of the tool in the spacer sleeve.

8. A surgical system comprising:
the surgical instrument according to claim 1; and
a tool configured to be received in the tool receptacle of the spacer sleeve of the surgical instrument,
the tool comprising:
    a part configured to be received in the spacer sleeve; and
    a magnetic memory comprising a layer that forms or coats a periphery of the part,
wherein the tool is adapted to cooperate with the surgical instrument such that the magnetic memory is read out via the readout device of the surgical instrument.

9. The surgical system according to claim 8, wherein the magnetic memory is configured to be slid onto the part of the tool.

10. The surgical system according to claim 8, wherein the magnetic memory comprises magnetized wire rings surrounding the periphery of the part, the magnetized wire rings being axially offset from each other along the tool.

11. The surgical system according to claim 8, wherein the magnetic memory comprises permanent magnets or wire pieces spaced from each other in a circumferential direction of the tool and in an axial direction along the tool.

12. The surgical system according to claim 8, wherein the magnetic memory comprises spherical permanent magnets arranged offset from each other in a circumferential direction of the tool and in an axial direction along the tool.

13. The surgical system according to claim 8, wherein the magnetic memory is read out upon rotation of the tool in the spacer sleeve.

* * * * *